United States Patent [19]

Hayashi et al.

[11] 4,256,757

[45] Mar. 17, 1981

[54] 1-SUBSTITUTED IMIDAZOLES FOR INHIBITION OF THROMBOXANE SYNTHETASE

[75] Inventors: Masaki Hayashi; Tadao Tanouchi, both of Takatsuki; Masanori Kawamura, Ibaraki; Ikuo Kajiwara, Takatsuki, all of Japan

[73] Assignees: Ono Pharmaceutical Co., Ltd.; Kissei Pharmaceutical Co., Ltd.

[21] Appl. No.: 35,181

[22] Filed: May 2, 1979

[30] Foreign Application Priority Data

May 2, 1978 [JP] Japan .................................. 53-52266

[51] Int. Cl.³ .................... A61K 31/415; C07D 233/60
[52] U.S. Cl. .......................... 424/273 R; 260/345.8 R; 260/345.9 R; 548/341
[58] Field of Search ...................... 548/341; 424/273 R

[56] References Cited

FOREIGN PATENT DOCUMENTS 2638470 3/1977 Fed. Rep. of Germany ........... 548/341

OTHER PUBLICATIONS

Burgess et al., Proc. Soc. Exptl. Biol. Med. 1930, vol. 28, pp. 115-11 6 (1930).
Novello et al., Chem. Abst. 1926, vol. 20, p. 3030.
Pailer et al., Monotshefte für Chemie 1977, vol. 108, pp. 1059-1066.

*Primary Examiner*—Henry R. Jiles
*Assistant Examiner*—Richard A. Schwartz
*Attorney, Agent, or Firm*—Sughrue, Rothwell, Mion, Zinn and Macpeak

[57] ABSTRACT

The imidazole derivatives of the general formula:

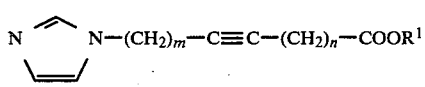

wherein $R^1$ represents a hydrogen atom, or a straight- or branched-chain alkyl group containing from 1 to 12 carbon atoms, the symbol $=$ represents a double bond that bond is E or Z, or a triple bond, and m and n, which may be the same or different, each represent zero, or an integer of 1 to 10, and non-toxic acid addition salts thereof, and, when $R^1$ represents a hydrogen atom, non-toxic salts thereof are new compounds. These compounds have a strong inhibitory effect on thromboxane synthetase from rabbit platelet microsomes, and are useful as therapeutically active agents for inflammation, hypertension, thrombus, cerebral apoplexy and asthma.

16 Claims, No Drawings

1-SUBSTITUTED IMIDAZOLES FOR INHIBITION OF THROMBOXANE SYNTHETASE

BACKGROUND OF THE INVENTION

1. Field of the Invention

THIS INVENTION relates to new imidazole derivatives, to a process for their preparation, and to pharmaceutical compositions containing them.

2. Description of the Prior Art

Up to now, of the compounds having an imidazole skeleton, it has been reported that imidazole and 1-methylimidazole possess an inhibitory action for thromboxane synthetase [Prostaglandins, 13(4), 611(1977)]. However, since their inhibitory action for thromboxane synthetase is weak, these compounds are hardly applicable as practically effective medicines.

On the other hand, N-(6-methoxycarbonylhexyl)imidazole has already been synthesized by P. Matthias et al, and publicly known [Monatsch Chem., 108(5), 1059(1977)]. Although that compound tends to have a stronger inhibitory effect on thromboxane synthetase when compared with imidazole or 1-methylimidazole, the inhibitory effect is not completely satisfactory as a practical medication.

Widespread investigations have been carried out in order to discover inter alia new imidazole derivatives possessing a much stronger and more specific inhibitory effect on thromboxane synthetase. As a result of extensive research and experimentation it has now been discovered that by introducing the double or triple bond or one or two alkyl groups to the 1-(ω-carboxy or alkoxycarbonylalkyl)imidazole, the pharmacological properties of the imidazole or 1-methylimidazole are enhanced.

DETAILED DESCRIPTION OF THE INVENTION

The present invention accordingly provides new imidazole derivatives of the general formula:

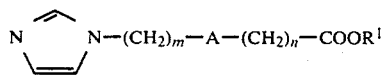
                                                        I wherein $R^1$ represents a hydrogen atom or a straight- or branched-chain alkyl group containing from 1 to 12 carbon atoms, A represents a C≡C group (in which the symbol ≡ represents a double bond that bond is E(i.e., trans) or Z(i.e., cis), or a triple bond), or a

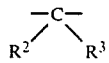

group (in which $R^2$ represents a hydrogen atom or a straight- or branched-chain alkyl group containing from 1 to 4 carbon atoms, and $R^3$ represents a straight- or branched-chain alkyl group containing from 1 to 10 carbon atoms), and m and n, which may be the same or different, each represent zero or an interger of 1 to 10, and non-toxic acid addition salts thereof, and, when $R^1$ represents a hydrogen atom, non-toxic salts thereof.

Especially, the present invention accordingly provides new imidazole derivatives of the general formula:

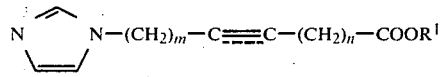
                                                        I' wherein the various symbols are as hereinbefore defined, and non-toxic acid addition salts thereof, and, when $R^1$ represents a hydrogen atom, non-toxic salts thereof.

Examples of the straight- or branched-chain alkyl group containing from 1 to 12 carbon atoms represented by $R^1$, are methyl, ethyl, propyl, butyl, pentyl, hexyl, heptyl, octyl, nonyl, decyl, undecyl, dodecyl and their isomers. Preferably $R^1$ is a hydrogen atom or a straight- or branched-chain alkyl group containing from 1 to 4 carbon atoms, most preferably a hydrogen atom or a methyl, ethyl or sec-butyl group.

Examples of the straight- or branched-chain alkyl group containing from 1 to 4 carbon atoms represented by $R^2$, are methyl, ethyl, propyl, isopropyl, butyl, isobutyl, sec-butyl, tert-butyl. Preferably $R^2$ is a hydrogen atom or a methyl group.

Examples of the straight- or branched-chain alkyl group containing from 1 to 10 carbon atoms represented by $R^3$, are methyl, ethyl, propyl, butyl, pentyl, hexyl, heptyl, octyl, nonyl, decyl and their isomers. Preferably $R^3$ is a methyl or butyl group.

Examples of the straight- chain alkylene group containing from 1 to 10 carbon atoms represented by $-(CH_2)_m-$ and $-(CH_2)_n-$, are methylene, ethylene, trimethylene, tetramethylene, pentamethylene, hexamethylene, heptamethylene, octamethylene, nonamethylene and decamethylene. Preferably m+n represents zero, or an integer of 1 to 10, most preferably zero, or an integer of 1 to 6.

According to the first feature of the present invention, the imidazole derivatives of general formula I, wherein the various symbols are as hereinbefore defined, are prepared by reacting a compound of the general formula:

$$X-(CH_2)_m-A-(CH_2)_n-COOR^1 \qquad II$$

wherein X represents a halogen atom, i.e. a fluorine, chlorine, bromine, iodine atom, and the other symbols are as hereinbefore defined with an imidazole silver salt or an imidazole alkali metal, e.g. sodium or potassium, salt in an inert organic solvent, e.g. benzene, toluene, xylene, dioxane, tetrahydrofuran(THF), acetonitrile, N,N-dimethylformamide, a lower alkanol such as ethanol or butanol, at a temperature from 0° to 150° C., preferably at a temperature from ambient to the reflux temperature of the reaction mixture.

If desired, products I may be purified by conventional means, e.g. by distillation at normal or reduced pressure, by thin layer, column or high-speed liquid chromatography on silica gel, or by recrystallization to give the pure imidazole derivatives.

Acids of the imidazole derivatives of general formula I, wherein $R^1$ represents a hydrogen atom, and the other symbols are as hereinbefore defined, may be prepared by saponification of the corresponding ester of general formula I, wherein $R^1$ is other than a hydrogen atom, by method known per se, for example by reaction with an aqueous solution of an alkali metal, e.g. sodium or potassium, or an alkaline earth metal, e.g. calcium or barium, hydroxide or carbonate, in the absence or in the presence of a water-miscible solvent such as an ether, e.g. dioxane or THF, or a lower alkanol, e.g. methanol or ethanol, at a temperature from −10° to 78° C. preferably at ambient temperature, or with an anhydrous solution of an alkali metal, e.g. sodium or potassium, hydroxide or carbonate in a lower alkanol such as methanol or ethanol at a temperature from −10° to 78° C. preferably at ambient temperature.

The imidazole metal salts may be prepared from imidazole by reaction with an alkali metal hydroxide such as sodium or potassium hydroxide, an alkali metal alkoxide such as sodium methoxide, an alkali metal carbonate such as sodium or potassium carbonate, an alkali metal hydride such as sodium or potassium hydride, or silver oxide in an inert solvent, e.g. benzene, toluene, xylene, dioxane, THF, acetonitrile, N,N-dimethylformamide, a lower alkanol such as ethanol or butanol, a crown ether, water, at a temperature from 0° to 100° C., preferably at a temperature from ambient to 90° C.

These metal salts may be used as an isolated compound or as a solution of the salts.

The compounds of general formula II, used as a starting material, are compounds known per se, or may easily be prepared by method known per se (i.e. compounds or methods heretofore used or described in the chemical literature). For example, compounds of general formula II, wherein A represents the $C\!\equiv\!C$ group, in which the symbol $\equiv$ represents the triple bond, or the

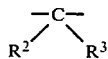

group, and the other symbols are as hereinbefore defined, may be prepared by the series of reactions depicted schematically below in Scheme A and B, wherein $R^4$ represents a hydrogen atom or a tetrahydropyran-2-yl group, THP represents the tetrahydropyran-2-yl group, p represents an integer of 3 to 10, q represents an integer of 1 to 10, r represents an integer of 2 to 10, Y represents a halogen atom, and the other symbols are as hereinbefore defined.

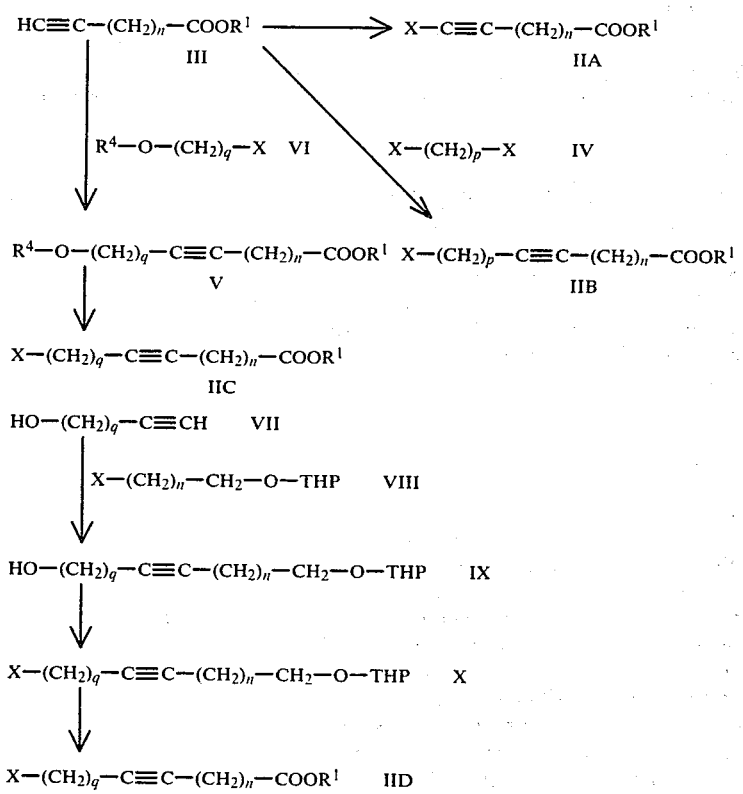

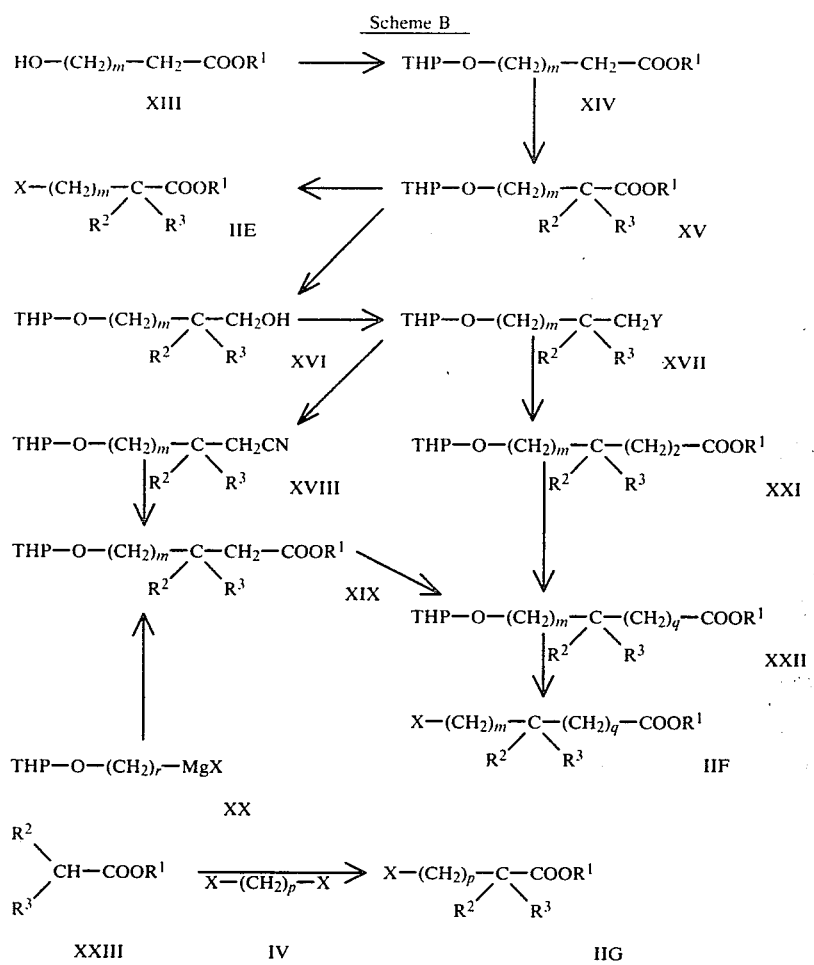

Scheme B

Referring to Scheme A, the conversion of compounds of general formula III to those of general formula IIA may be carried out by the method described in J. Amer. Chem. Soc., 85, 1648(1963).

Compounds of general formula IIB may be prepared from compounds of general formula III by reaction with a lithioating agent such as butyl lithium or lithium diisopropylamide in an inert organic solvent, e.g. THF, at a temperature below room temperature, followed by reaction of the resulting lithium compound with a compound of general formula IV to give compounds of general formula IIB.

Compounds of general formula V may be prepared from the lithium compound of compounds of general formula III by reaction with a compound of general formula VI in an inert organic solvent, e.g. THF or hexamethylphosphoramide at a moderately low temperature, preferably below room temperature.

Compounds of general formula V, wherein $R^4$ represents a hydrogen atom, may be prepared from a compound of general formula V, wherein $R^4$ represents a tetrahydropyran-2-yl group, by mild hydrolysis under acidic conditions with (1) an aqueous solution of an organic acid such as acetic acid, propionic acid, oxalic acid or p-toluenesulphonic acid, or an aqueous solution of an inorganic acid such as hydrochloric acid, sulphuric acid or phosphoric acid, advantageously in the presence of an inert organic solvent miscible with water, e.g. a lower alkanol such as methanol or ethanol, preferably methanol, or an ether such as 1,2-dimethoxyethane, dioxane or THF, preferably THF, at a temperature from ambient to 75° C., preferably below 45° C., or (2) an anhydrous solution of an organic acid such as p-toluenesulphonic acid or trifluoroacetic acid in a lower alkanol such as methanol or ethanol at a temperature from 10° to 45° C., or (3) an anhydrous solution of p-toluenesulphonic acid-pyridine complex in a lower alkanol such as methanol or ethanol at a temperature from 10° to 60° C.

Compounds of general formula V, wherein $R^4$ represents a hydrogen atom, may also be prepared by the method described in J. Chem. Soc., 5889(1963).

Compounds of general formula IIC may be prepared from compounds of general formula V, wherein $R^4$ represents a hydrogen atom, by methods known per se for the conversion of a hydroxyl group to a halogen atom (optionally via an arylsulphonyloxy or alkylsulphonyloxy group), for example, by methods described in 'Compendium of Organic Synthetic Methods', volume 1 (1971), 2(1974) and 3(1977), Section 138, Wiley-Interscience (USA) (hereinafter used these books as the Reference A).

Compounds of general formula X may be prepared from compounds of general formula VII via compounds of general formula IX by means heretofore mentioned for the conversion of compounds of general formula III to those of general formula IIC.

Compounds of general formula IID, wherein $R^1$ represents a hydrogen atom, may be prepared by hydrolysis the tetrahydropyran-2-yl group of compounds of general formula X to a hydroxyl group by means heretofore mentioned for the conversion of compounds of general formula V, wherein $R^4$ represents a tetrahydropyran-2-yl group, to those of general formula V, wherein $R^4$ represents a hydrogen atom, followed by the oxidation of the obtained hydroxyl compounds with the Jones reagent or by methods described in Section 18 of the Reference A. If desired, the products, thus obtained, may be esterified by methods known per se, for example, by treatment with a diazoalkane containing from 1 to 12 carbon atoms in an inert organic solvent, e.g. diethyl ether, ethyl acetate, methylene chloride, acetone, or a mixture of two or more of them, at a temperature from ambient to $-10°$ C., preferably 0° C., to give compounds of general formula IID, wherein $R^1$ is other than a hydrogen atom.

Referring to Scheme B, the conversion of compounds of general formula XIII to those of general formula XIV may be carried out by reaction with 2,3-dihydropyran in an inert organic solvent, e.g. methylene chloride, in the presence of an acid-catalyst, e.g. p-toluenesulphonic acid, sulphuric acid, trifluoroborane-etherate, phosphorus oxychloride, at a temperature of ambient to 0° C., preferably ambient temperature.

Compounds of general formula XV, wherein $R^2$ represents a hydrogen atom, may be prepared from compounds of general formula XIV by means heretofore mentioned for the conversion of compounds of general formula III to their lithium compounds, followed by reaction of the resulting lithium compound with a compound of the general formula:

$$R^3\text{-}Z \qquad\qquad\qquad \text{XXIV}$$

wherein Z represents a halogen atom, and $R^3$ is as hereinbefore defined to give compounds of general formula XV, wherein $R^2$ represents a hydrogen atom.

Compounds of general formula XV, wherein $R^2$ represents a straight- or branched-chain alkyl group containing from 1 to 4 carbon atoms, may be prepared from compounds of general formula XV, wherein $R^2$ represents a hydrogen atom, by means heretofore mentioned for the preparation of compounds of general formula XV, wherein $R^2$ represents a hydrogen atom, but replacing compounds of general formula XXIV by a compound of the general formula:

$$R^5\text{-}Z \qquad\qquad\qquad \text{XXV}$$

wherein $R^5$ represents a straight- or branched-chain alkyl group containing from 1 to 4 carbon atoms and Z is as hereinbefore defined.

The conversion of compounds of general formula XV to those of general formula IIE may be carried out by means heretofore mentioned for the conversion of compounds of general formula V, wherein $R^4$ represents a tetrahydropyran-2-yl group, to those of general formula IIC. Compounds of general formula XVI may be prepared from compounds of general formula XV by methods described in Section 32 or 38 of the Reference A, and converted to compounds of general formula XVII by means heretofore mentioned for the conversion of compounds of general formula V, wherein $R^4$ represents a hydrogen atom, to those of general formula IIC.

Compounds of general formula XIX may be prepared from compounds of general formula XVII via compounds of general formula XVIII by methods described in Section 190 and 28 or 118 of the Reference A.

Compounds of general formula XIX, wherein m represents an integer of 2 to 10, may also be prepared from compounds of general formula XX by the Grignard reaction with a compound of the general formula:

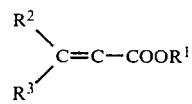

wherein the various symbols are as hereinbefore defined in an inert organic solvent, e.g. diethyl ether, THF, in the presence of cuprous chloride at a temperature from ambient to 0° C.

Compounds of general formula XXI may be prepared from compounds of general formula XVII by methods described in Section 25 or 115 of the Reference A.

Compounds of general formula XXII may be prepared from compounds of general formula XIX or XXI by means heretofore mentioned for the conversion of compounds of general formula XV to those of general formula XIX or XXI.

The conversion of compounds of general formula XXII to those of general formula IIF may be carried out by means heretofore mentioned for the conversion of compounds of general formula V, wherein $R^4$ represents a tetrahydropyran-2-yl group, to those of general formula IIC.

Compounds of general formula IIE, wherein m represents an integer of 3 to 10, i.e. compounds of general formula IIG may also be prepared from compounds of general formula XXIII by means heretofore mentioned for the conversion of compounds of general formula III to their lithium compounds, followed by reaction of the resulting lithium compounds with compounds of general formula IV to give compounds of general formula IIG.

The compounds, used as a starting material in Scheme A and B, are compounds known per se, or may easily be prepared by methods known per se.

Compounds of general formula II, wherein A represents the C≡C group, in which the symbol ≡ represents the double bond that bond is E or Z, and the other symbols are as hereinbefore defined, may easily be prepared from compounds of general formula II, wherein A represents the C≡C group, in which the symbol ≡ represents the triple bond, i.e. compounds of general formula IIA, IIB, IIC or IID by methods described in Section 196 of the Reference A.

According to the second feature of the present invention, the imidazole derivatives of general formula I, wherein A represents the C≡C group, in which the symbol ≡ represents the double bond, and the other symbols are as hereinbefore defined, i.e. compounds of the general formula:

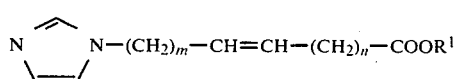

wherein the double bond is E (i.e. trans) or Z (i.e. cis), and the other symbols are as hereinbefore defined may be prepared from compounds of general formula I, wherein A represents the C≡C group, in which the symbol ≡ represents the triple bond, and the other symbols are as hereinbefore defined, i.e. compounds of the general formula:

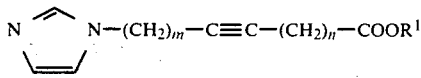  IB wherein the various symbols are as hereinbefore defined by methods described in Section 196 of the Reference A.

According to the third feature of the present invention, the imidazole derivatives of general formula I, wherein m represents an integer of 2 to 10, A represents the C=C group, in which the symbol = represents the double bond that double bond is E or Z, and the other symbols are as hereinbefore defined, i.e. compounds of the general formula:

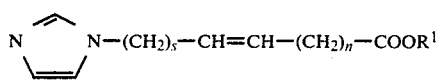  IC wherein s represents an integer of 2 to 10, and the other symbols are as hereinbefore defined may be prepared by the Wittig reaction of a compound of the general formula:

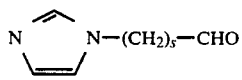  XXVII wherein s is as hereinbefore defined with a phosphorane compound of the general formula:

(R$^6$)hd 3P=CH(CH$_2$)$_n$—COOR$^1$   XXVIII wherein R$^6$ represents a phenyl group unsubstituted or substituted by a lower alkyl group containing from 1 to 4 carbon atoms, preferably an unsubstituted phenyl group, or a lower alkyl group containing from 1 to 6 carbon atoms, preferably butyl, or the cyclohexyl group, and n and R$^1$ are as hereinbefore defined.

Compounds of general formula IC, wherein n represents zero, the double bond is E and the other symbols are as hereinbefore defined, may also be prepared from compounds of general formula XXVII by the Wittig reaction with the sodium derivatives of a dialkylphosphonate of the general formula:

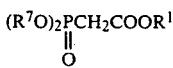  XXIX wherein R$^7$ represents a lower alkyl group containing from 1 to 4 carbon atoms, preferably methyl or ethyl, and R$^1$ is as hereinbefore defined, obtained by the reaction of a dialkylphosphonate of general formula XXIX with sodium hydride.

The Wittig reaction is effected in an inert organic solvent, e.g. an ether such as diethyl ether, THF, dioxane or 1,2-dimethoxyethane, a hydrocarbon such as benzene, toluene, xylene or hexane, a dialkyl sulphoxide such as dimethyl sulphoxide, a dialkylformamide such as N,N-dimethylformamide, a halogenated hydrocarbon such as methylene chloride or chloroform, or a lower alkanol such as methanol or ethanol at a temperature from −78° C. to the reflux temperature of reaction mixture.

The phosphorane compounds of general formula XXVIII and the dialkyl phosphonates of general formula XXIX may be prepared by methods known per se.

The formyl compounds of general formula XXVII may be prepared from a compounds of the general formula:

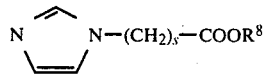  XXX wherein R$^6$ represents a lower alkyl group containing from 1 to 4 carbon atoms, or a hydrogen atom, and s is as hereinbefore defined by methods described in Section 47 or 53 of the Reference A, or prepared from a compound of the general formula:

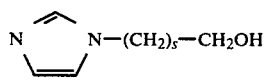  XXXI wherein s is as hereinbefore defined by methods described in Section 48 of the Reference A.

Compounds of general formula XXX and XXXI may be prepared by the methods described in the following patent applications: Japanese Patent Applications Nos. 53-17238, 53-18053, 53-18054 and 53-18340, i.e.;

From Japanese Patent Application No. 53-17238:

The imidazole compounds of this invention (i.e., No. 53-17238) of the general formula (I) (the formula (I) is previously defined in the specification as follows:

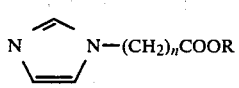  (I)

wherein R is a lower alkyl group and n is an integer of 3 to 5), can be prepared by reacting imidazole of the formula:

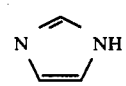  (II)

with a compound of the general formula:

X(CH$_2$)$_n$COOR   (III)

wherein X is an acid residual group and n and R are as hereinbefore defined. In this case, imidazole of the formula (II) used as starting material is well known and can easily be prepared by methods described in the literature. The compounds of the general formula (III) are also known compounds and can also easily be prepared by methods described in the literature.

The above-mentioned reaction may be carried out by heating imidazole of the formula (II) with a compound of the general formula (III) in the presence of a base in an inert organic solvent.

Advantageously the reaction can be carried out by dissolving or suspending a base in an equimolar amount to imidazole of the formula (II) in an inert organic solvent, adding imidazole of the formula (II) to the above mixture with stirring, and then heating for 10 minutes to 2 hours. Subsequently the compound of the general formula (III) in a proportion of 0.9 to 1.0 mol per mol of imidazole of the formula (II) is added to the reaction mixture, the mixture is heated to 50° to 150° C. for 10 minutes to 5 hours, and then the reaction product is concentrated under reduced pressure, the residue is purified by distillation to obtain the desired product.

From Japanese Patent Application No. 53-18053:

The imidazole compounds of this invention (i.e., No. 53-18053) of the general formula (I) (the formula (I) is previously defined in the specification as follows:

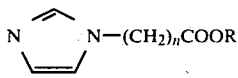   (I)

wherein R is a lower alkyl group and n is an integer of 7 to 20), can be prepared by reacting imidazole of the formula:

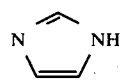   (II)

with a compound of the general formula:

X(CH$_2$)$_n$COOR   (III)

wherein X is an acid residual group and n and R are as hereinbefore defined. In this case, imidazole of the formula (II) used as a starting material is well known and can easily be prepared methods described in the literature. The compounds of the general formula (III) are also known compounds and can also easily be prepared by methods described in the literature.

The above-mentioned reaction may be carried out by heating imidazole of the formula (II) with a compound of the general formula (III) in the presence of a base in an inert organic solvent.

Advantageously the reaction can be carried out by dissolving or suspending a base in an equimolar amount to imidazole of the formula (II) in an inert organic solvent, adding imidazole of the formula (II) to the above mixture with stirring, and then heating for 10 minutes to 2 hours. Subsequently the compound of the general formula (III) in a proportion of 0.9 to 1.0 mol per mol of imidazole of the formula (II) is added to the reaction mixture, the mixture is heated to 50° to 150° C. for 10 minutes to 5 hours, and then the reaction proudct is concentrated under reduced pressure, the residue is purified by distillation to obtain the desired product.

From Japanese Patent Application No. 53-18054:

In the general formula (I) (the formula (I) is previously defined in the specification as follows:

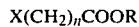   (I)

wherein R is a carbamoyl, amino, hydroxyl or cyano group), the term "alkylene" means a straight-chain alkylene group containing from 1 to 20 carbon atoms, preferably from 3 to 11 carbon atoms. The compounds of the general formula (I) wherein R is a hydroxyl group, i.e. the compounds of the general formula:

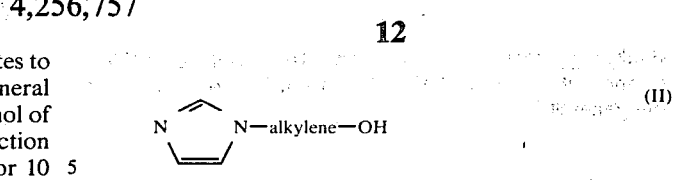   (II)

can be prepared, for example, by reacting imidazole with a lower alkyl ester of saturated fatty acid having an acid residual group at the end of the chain to obtain imidazole carboxylate of the general formula:

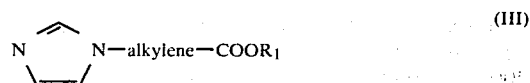   (III)

wherein R$_1$ is a lower alkyl group, and then reducing compounds obtained above. Examples of the acid residual groups attached to the end of the lower alkyl ester of saturated fatty acids, used as starting materials are halogen atoms and acid residual groups formed from organic sulfonic acid. The reduction of an ester group to a hydroxyl group can be carried out by using metal hydride compounds such as lithium aluminum hydride.

From Japanese Patent Application No. 53-18340:

The present invention (i.e., No. 53-18340) accordingly provides the compounds of the general formula (I) (the formula (I) is previously defined in the specification as follows:

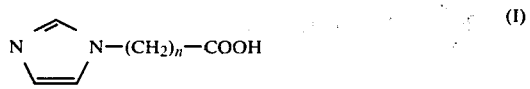   (I)

wherein n is an integer of from 3 to 20). The symbol "n" as used herein means an integer of from 3 to 20, preferably 5 to 11.

Such compounds can be prepared, for example, by reacting imidazole with a ω-substituted fatty acid of the general formula:

Y—(CH$_2$)$_n$—COOH   (II)

wherein Y is an acid residual group such as a halogen atom or an acid residual group formed from organic sulfonic acid, and n is as hereinbefore defined, in an inert organic solvent in the presence of chlorine with heating. Also, the compound of the general formula (I) can be prepared by reacting imidazole with an ester of the ω-substituted fatty acid of the general formula:

Y—(CH$_2$)$_n$—COOR   (III)

wherein R is a lower alkyl group and the others are hereinbefore defined, or a nitrile of the ω-substituted fatty acid of the general formula:

Y—(CH$_2$)$_n$—CN   (IV)

wherein n and Y are hereinbefore defined, instead of compounds of the general formula (II), and then hydrolyzing the resulting product by conventional methods.

When using an ester of the general formula (III) as a starting material, the reaction can be carried out by dissolving or suspending a base in an equimolar amount to imidazole, in an inert organic solvent, adding imidazole to the above mixture with stirring and then heating for 10 minutes to 2 hours. Subsequently the ester of the general formula (III) in a proportion of 0.9 to 1.0 mol per mol of imidazole is added to the reaction mixture, the reaction mixture is heated to 50° to 150° C. for 10 minutes to 5 hours, and then the reaction product is concentrated under reduced pressure, the residue is purified by distillation. N-(ω-alkoxycarbonylalkyl-)imidazole thus obtained, is hydrolyzed for the conversion of a terminal ester group to a carboxy group by conventional methods to obtain the desired products.

When using a nitrile of the general formula (IV) as a starting material, the reaction can be carried out by means heretofore mentioned for the reaction using an ester of the general formula (III).

In the above reaction, a metal hydride compound such as sodium hydride, an organic tertiary base such as triethylamine, an alcoholate such as sodium methoxide, a salt of alkali metal such as sodium carbonate, etc. can be used as a base. Examples of inert organic solvents include dimethylformamide, toluene, xylene, benzene, alcohol, etc.

Imidazole, ω-substituted fatty acids, their esters and nitriles used as starting materials are well known and can easily be prepared by methods known per se.

According to the fourth feature of the present invention, the imidazole derivatives of general formula I, wherein A represents the

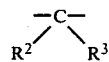

group, m represents an integer of 3 to 10, n represents zero, and the other symbols are as hereinbefore defined, i.e. compounds of the general formula:

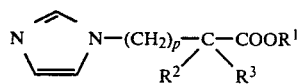
ID wherein the various symbols are as hereinbefore defined, may be prepared by reaction of a compound of the general formula:

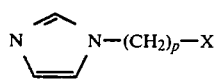
XXXII wherein p and X are as hereinbefore defined with a lithium compound of compounds of the general formula:

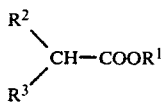
XXXIII wherein the various symbols are as hereinbefore defined by means heretofore mentioned for the conversion of compounds of general formula III to those of general formula IIB.

Compounds of general formula XXXII may be prepared by reaction of an imidazole metal salt with compounds of general formula IV by means heretofore mentioned for the conversion of compounds of general formula II to those of general formula I.

Compounds of general formula XXXIII may be prepared by methods known per se.

According to the fifth feature of the present invention, the imidazole derivatives of general formula I, wherein A represents the

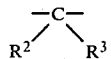

group, n represents an integer of 2 to 10, and the other symbols are as hereinbefore defined, i.e. compounds of the general formula:

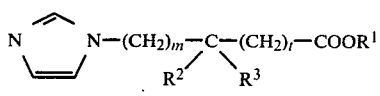
IE wherein t represents an integer of 2 to 10, and the other symbols are as hereinbefore defined may be prepared by catalytic reduction of a compound of the general formula:

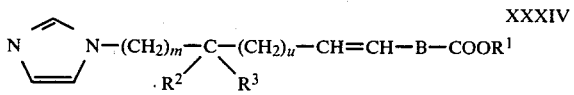
XXXIV wherein u represents zero or an integer of 1 to 8, B represents a single bond, or an unsaturated or saturated straight-chain alkylene group containing from 1 to 8 carbon atoms, but the carbon number of the group —(CH$_2$)$_u$—CH=CH—B— are an integer of 2 to 10, the double bond is E or Z or their mixture, and the other symbols are as hereinbefore defined.

Suitably, the catalytic reduction may be effected by hydrogenation in the presence of a hydrogenation catalyst, for example palladium on charcoal, palladium black or platinum dioxide, in an inert organic solvent, e.g. a lower alkanol containing from 1 to 4 carbon atoms such as methanol or ethanol, at laboratory temperature at normal or elevated pressure, e.g. at a hydrogen pressure from atmospheric to 15 kg/cm$^2$.

Compounds of general formula XXXIV may be prepared by the Wittig reaction of a compound of general formula:

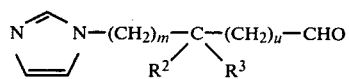
XXXV wherein the various symbols are as hereinbefore defined with a phosphorane compound of the general formula:

(R$^6$)$_3$P=CH—B—COOR$^1$   XXXVI wherein the various symbols are as hereinbefore defined, or with a sodium derivative of compounds of general formula XXIX, or with a lithium or sodium derivative of compounds of the general formula:

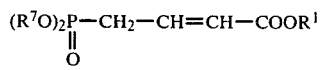
XXIXA wherein the double bond is E or Z, and the other symbols are as hereinbefore defined (obtained from a compound of general formula XXIXA with sodium hydride or lithium diisopropylamide) by means heretofore mentioned for the conversion of compounds of general formula XXVII to those of general formula IC.

Compounds of general formula XXXV may be prepared from compounds of general formula I, wherein n represents zero, or an integer of 1 to 8, by means heretofore mentioned for the conversion of compounds of general formula XXX to those of general formula XXVII.

Compounds of general formula XXXV, wherein m represents zero, and n represents 1, may also be prepared by reaction of a compound of the general formula:

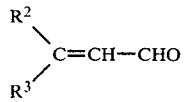

XXXVII wherein $R^2$ and $R^3$ are as hereinbefore defined with imidazole in an inert organic solvent, e.g. acetonitrile, at ambient temperature.

Compounds of general formula XXXV, wherein $R^2$ represents a hydrogen atom, m represents 1, and n represents zero, may also be prepared by reaction of a compound of the general formula:

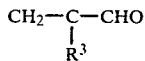

XXXVIII wherein $R^3$ is as hereinbefore defined with imidazole in an inert organic solvent, e.g. acetonitrile, at ambient temperature.

Compounds of general formula I, wherein $R^1$ represents a hydrogen atom, may, if desired, be converted by methods known per se into salts. Preferably the salts are non-toxic salts. By the term 'non-toxic salts' as used in this specification, is meant salts the cations (or in the case of acid addition salts referred to hereinafter the anions) of which are relatively innocuous to the animal organism when used in therapeutic doses so that the beneficial pharmacological properties of the compounds of general formula I are not vitiated by side-effects ascribable to those cations (or anions). Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing 2 or 3 carbon atoms. Suitable non-toxic amine salts are, e.g. tetraalkylammonium salts such as tetramethylammonium salts, and other organic amine salts such as methylamine salts, dimethylamine salts, cyclopentylamine salts, benzylamine salts, phenethylamine salts, piperidine salts, monoethanolamine salts, diethanolamine salts, lysine salts and arginine salts.

Salts may be prepared from the acids of general formula I, wherein $R^1$ represents a hydrogen atom, by methods known per se, for example by reaction of stoichiometric quantities of an acid of general formula I and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary after removal of part of the solvent.

The imidazole derivatives of general formula I may, if desired, be converted by methods known per se into acid addition salts, which are preferably non-toxic as hereinbefore defined.

Acid addition salts may be prepared from compounds of general formula I by methods known per se, for example by reaction of stoichiometric quantities of a compound of general formula I and the appropriate acid in a suitable solvent. The acid addition salts may be purified by recrystallisation from a suitable solvent or suitable mixture of two or more solvents. Suitable non-toxic acid addition salts are the salts with inorganic acids such as hydrochloric acid, hydrobromic acid, hydroiodic acid, sulphuric acid, phosphoric acid and nitric acid, or an organic acid such as acetic acid, propionic acid, lactic acid, tartaric acid, citric acid, methanesulphonic acid, ethanesulphonic acid, benzenesulphonic acid, toluenesulphonic acid, isethionic acid and succinic acid.

The imidazole derivatives of the general formula I of this invention exhibit an inhibitory action for thromboxane synthetase from rabbit platelet microsomes. That is, the imidazole derivatives of this invention inhibit conversion of prostaglandin $H_2$ into thromboxane $B_2$ via thromboxane $A_2$ which is an unstable intermediate, and which is known to induce irreversible platelet aggregation and to contract smooth muscle and particularly a blood vessel muscle [Nature, 261(6), 17(1976)]. These results demonstrate that the imidazole derivatives of this invention inhibit the biosynthesis of thromboxane $A_2$, and are thus useful for treatment of diseases caused by thromboxane $A_2$, such as inflammation, hypertension, thrombus, cerebral apoplexy and asthma.

The inhibitory action of the imidazole derivatives of this invention can be confirmed by determination of the thromboxane $B_2$ produced by thromboxane synthetase from prostaglandin $H_2$ via thromboxane $A_2$. Furthermore, the inhibitory action of the imidazole derivatives of this invention can be confirmed by determination of the inhibitory effect on platelet aggregation caused by arachidonic acid (arachidonic acid is converted to prostaglandin $H_2$ by cyclooxygenase, and prostaglandin $H_2$ is converted to thromboxane $B_2$ via thromboxane $A_2$ which is known to induce platelet aggregation as described above). Further still, the inhibitory action of the imidazole derivatives of this invention can be confirmed by determination of the inhibitory effect on sudden deaths caused by arachidonic acid.

For example, in standard laboratory tests, (E)-1-(7-ethoxycarbonyl-6-heptenyl)imidazole, (E)-1-(7-carboxy-6-heptenyl)imidazole hydrochloride, 1-(7-carboxy-6-heptynyl)imidazole hydrochloride, 1-(7-carboxy-2-heptynyl)imidazole hydrochloride, (Z)-1-(7-carboxy-2-heptenyl)imidazole hydrochloride, (Z)-1-(7-carboxy-6-heptenyl)imidazole hydrochloride, 1-[(7RS)-7-ethoxycarbonyloctyl]imidazole, 1-(7-ethoxycarbonyl-7-methyloctyl)imidazole, 1-[(7RS)-7-carboxyoctyl]imidazole hydrochloride, 1-(7-carboxy-7-methyloctyl- )imidazole hydrochloride, 1-[(6RS)-7-carboxy-6-methylheptyl]imidazole hydrochloride, 1-[(4RS)-4-ethoxycarbonyloctyl]imidazole, 1-(7-carboxy-1,1-dimethylheptyl)imidazole hydrochloride and 1-(7-carboxy-5,5-dimethylheptyl)imidazole hydrochloride produce a 50% inhibition of thromboxane synthetase from rabbit platelet microsomes at the molar concentrations of $2.8 \times 10^{-6}$, $7.0 \times 10^{-8}$, $3.0 \times 10^{-8}$, $5.6 \times 10^{-8}$, $1.6 \times 10^{-8}$, $2.0 \times 10^{-7}$, $1.0 \times 10^{-6}$, $3.0 \times 10^{-8}$, $3.0 \times 10^{-8}$, $4.8 \times 10^{-8}$, $1.3 \times 10^{-7}$, $9.0 \times 10^{-8}$ and $7.1 \times 10^{-8}$, respectively, 1-(7-carboxy-6-heptynyl)imidazole hydrochloride, 1-(7-carboxy-2-heptynyl)imidazole hydrochloride, 1-[(7RS)-7-ethoxycarbonyloctyl]imidazole, 1-(7-ethoxycarbonyl-7-methyloctyl)imidazole, 1-[(7RS)-7-carboxyoctyl]imidazole hydrochloride, 1-(7-carboxy-7-methyloctyl)imidazole hydrochloride, 1-[(6RS)-7-carboxy-6-methylheptyl]imidazole hydrochloride and 1-(7-carboxy-1,1-dimethylheptyl)imidazole hydrochloride produce a 50% inhibition of arachidonic acid-induced blood platelet aggregation in platelet-rich plasma of rats at the concentrations of 4.0 μg/ml, $2.1 \times 10^{-1}$ μg/ml, $5.2 \times 10^{-2}$ μg/ml, $4.4 \times 10^{-1}$ μg/ml, $1.7 \times 10^{-1}$ μg/ml, $9.1 \times 10^{-2}$ μg/ml, $5.3 \times 10^{-1}$ μg/ml and $1.8 \times 10^{-1}$ μg/ml, respectively, in comparison with controls, and 1-(7-carboxy-2-heptynyl)imidazole hydrochloride, 1-[(7RS)-7-carboxyoctyl]imidazole hydrochloride and 1(7-carboxy-7-methyloctyl)imidazole hydrochloride produce an inhibitory effect on arachidonic acid-induced sudden deaths of rabbits by oral administration at the doses of 100 mg/kg animal body weight, respectively.

In acute toxicity tests, the $LD_{50}$ value of 1-[(7RS)-7-carboxyoctyl]imidazole hydrochloride and 1-(7-carboxy-7-methyloctyl)imidazole hydrochloride, determined in ICR-stain male mice (7 weeks old) by intravenous administration, was 540 mg/kg and 330 mg/kg, respectively.

The imidazole derivatives including within the present invention are those, which introduced one double or triple bond, or one or two alkyl group into 1-(carboxymethyl)imidazole (when A represents the

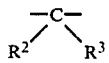

group in formula I), 1(2-carboxyethyl)imidazole, 1-(3-carboxypropyl)imidazole, 1-(4-carboxybutyl)imidazole, 1-(5-carboxypentyl)imidazolo, 1-(6-carboxyhexyl)imidazolo, 1-(7-carboxyheptyl)imidazole, 1-(8-carboxyoctyl)imidazole, 1-(9-carboxynonyl)imidazole, 1-(10-carboxydecyl)imidazole, 1-(11-carboxyundecyl)imidazole, 1-(12-carboxydodecyl)imidazole, 1-(13-carboxytridecyl)imidazole, 1-(14-carboxytetradecyl)imidazole, 1-(15-carboxypentadecyl)imidazole, 1-(16-carboxyhexadecyl)imidazole, 1-(17-carboxyheptadecyl)imidazole, 1-(18-carboxyoctadecyl)imidazole, 1-(19-carboxynonadecyl)imidazole, 1-(20-carboxyeicosanyl)imidazole, 1-(21-carboxyheneicosanyl)imidazole, 1-(22carboxydocosanyl)imidazole (when A represents the $C \equiv C$ group in formula I), and esters, non-toxic salts and non-toxic acid addition salts thereof.

Preferred imidazole derivatives of the present invention are the esters: (E)-1-(7-ethoxycarbonyl-6-heptenyl)imidazole, 1-(7-methoxycarbonyl-6-heptenyl)imidazole, 1-(7-methoxycarbonyl-2-heptynyl)imidazole, (Z)-1-(7-methoxycarbonyl-2-heptenyl)imidazole, (Z)-1-(7-methoxycarbonyl-6-heptenyl)imidazole, 1-[(7RS)-7-ethoxycarbonyloctyl]imidazole, 1-(7-ethoxycarbonyl-7-methyloctyl)imidazole, 1-[(6RS)-7-sec-butoxycarbonyl-6-methylheptyl]imidazole, 1-[(4RS)-4-ethoxycarbonyloctyl]imidazole, 1-[(1RS)-6methylhexyl]imidazole, 1-[(2RS)-6-methoxycarbonyl-2-methylhexyl]imidazole, 1-(3-ethyoxycarbonyl-1,1-dimethylpropyl)imidazole, 1-(7-ethoxycarbonyl-1,1-dimethylheptyl)imidazole, 1-(7-methoxycarbonyl-5,5-dimethylheptyl)imidazole, 1-(1-ethoxycarbonyl-1-methylethyl)imidazole, 1-(5-ethoxycarbonyl-5-methylhexyl)imidazole, and their non-toxic acid addition salts, and the acids: (E)-1-(7-carboxy-6-heptenyl)imidazole, 1-(7-carboxy-6-heptnyl)imidazole, 1-(7-carboxy-2-heptynyl)imidazole, (Z)-1-(7-carboxy-2-heptenyl)imidazole, (Z)-1-(7-carboxy-6-heptenyl)imidazole, 1-[(7RS)-7-carboxyoctyl]imidazole, 1-(7-carboxy-7-methyloctyl)imidazole, 1-[(6RS)-7-carboxy-6-methylheptyl]imidazole, 1-[(4RS)-4-carboxyoctyl]imidazole, 1-[(1RS)-6-carboxy-1-methylhexyl]imidazole, 1-[(2RS)-6-carboxy-2-methylhexyl]imidazole, 1-(3-carboxy-1,1-dimethylpropyl)imidazole, 1-(7-carboxy-1,1-dimethylheptyl)imidazole, 1-(7-carboxy-5,5-dimethylheptyl)imidazole, and their non-toxic salts and non-toxic acid addition salts.

The following Reference Examples and Examples illustrate, but not limit, the preparation of new imidazole derivatives of the present invention. In the Reference Examples and Examples 'TLC', 'IR', 'NMR' and 'MS' represent respectively 'Thin layer chromatography', 'Infrared absorption spectrum', 'Nuclear magnetic resonance spectrum' and 'Mass spectrum'. Where solvent ratios are specified, e.g. in chromatographic separations, the ratios are by volume. The solvents in parentheses show the developing solvent used in the thin layer chromatography. Except when specified otherwise, infrared spectra are recorded by the liquid film method, and nuclear magnetic resonance spectra are recorded in deuterochloroform ($CDCl_3$) solution.

REFERENCE EXAMPLE 1

1-(5-formylpentyl)imidazole

Under an atmosphere of nitrogen, 8.8 ml of a 25% (W/V) solution of diisobutylaluminum hydride in toluene was added dropwise to a solution of 2.50 g of 1-(5-ethoxycarbonylpentyl)imidazole in 120 ml of toluene at $-70°$ C., and the mixture was stirred at the same temperature for 30 minutes. To the reaction mixture was added one ml of methanol at $-70°$ C.; and one ml of water at 0° C., then the mixture was stirred at 30° C. for one hour. The reaction mixture was filtered, the filtrate was dried over magnesium sulphate and concentrated under reduced pressure. The residue was purified by column chromatography on silica gel using a mixture of chloroform and methanol (25:1) as eluent to give 1.15 g of the title compound having the following physical characteristics:

TLC(chloroform:methanol=9:1): Rf=0.40.

IR: $\nu=3120$, 2950, 2870, 2735, 1730, 1505, 1455, 1235, 1110, 1080 $cm^{-1}$.

NMR: $\delta=9.45(1H,t)$, 7.30(1H,m), 6.90(1H,m), 6.77(1H,m), 3.86(2H,t), 2.40(2H, t), 2.05–1.00(8H,m).

MS(%): m/e=165(M-1,25), 138(31), 111(75), 82(100), 81(50), 69(45), 55(50), 54(45).

REFERENCE EXAMPLE 2

8-bromo-6-octynoic acid methyl ester

To a solution of 2.1 g of 8-bromo-6-octyn-1-ol(prepared as described hereafter) in 20 ml of acetone was added dropwise 7.7 ml of a Jones reagent (prepared by dissolving 6.5 g of chromium trioxide in 5.75 ml of conc. sulphuric acid diluted with water to a volume of 25 ml) at 2° to 5° C. over a period of 40 minutes. To it was added 3 ml of isopropanol. The reaction mixture was diluted with diethyl ether, washed with water, a saturated aqueous solution of sodium chloride, dried over magnesium sulphate and concentrated under reduced pressure to give crude 8-bromo-6-octynoic acid. The crude product, thus obtained, was dissolved in 20 ml of diethyl ether, and diazomethane-etherate was added with cooling in an ice bath until the solution was coloured pale yellow. The reaction mixture was concentrated under reduced pressure. The residue was purified by column chromatography on silica gel using a mixture of benzene and ethyl acetate (50:1) as eluent to give 1.583 g of the title compound having the following physical characteristics:

TLC(benzene:ethyl acetate = 50:1): Rf=0.43;

IR: $\nu$=3020, 2960, 2875, 2245, 1740, 1435, 1220, 1080 cm$^{-1}$.

NMR: $\delta$=3.88(2H,t), 3.63(3H,s), 2.6–2.0(4H,m), 2.0–1.1(4H,m).

MS(%): m/e=235(1), 233(1), 203(5.5), 201(5.5), 174(3.5), 172(3.5), 153(100), 121(30.5), 93(91.5), 79(79.5), 77(42.5).

8-bromo-6-octyn-1-ol, used as a starting material in the above procedure, was prepared from 5-bromopentan-1-ol [described in 'Tetrahedron', 27,5979(1971)] as follows:

(1) 5-bromo-1-(tetrahydropyran-2-yloxy)pentane

To 36 g of 5-bromopentan-1-ol were added 24.72 ml of 2,3-dihydropyran and 3 drops of phosphorus oxychloride under cooling in an ice bath, and the mixture was stirred overnight at room temperature. The reaction mixture was diluted with diethyl ether, washed with 5% aqueous potassium hydroxide, water, a saturated aqueous solution of sodium chloride, dried over magnesium sulphate and concentrated under reduced pressure. The residue was purified by column chromatography on silica gel using a mixture of ethyl acetate and hexane (1:19) as eluent to give 49.5 g of the subtitle compound having the following physical characteristics:

TLC(benzene:ethyl acetate=4:1): Rf=0.79;

IR: $\nu$=2960, 2900, 1460, 1450, 1365, 1145, 1130, 1040, 1030, 980, 820, 780 cm$^{-1}$.

NMR:$\delta$=4.5(1H,m), 4.1–3.1(6H,m), 2.5–1.1(12H,m).

MS(%): m/e=250(5), 151(9.5), 149(10), 85(100), 69(37).

(2) 8-(tetrahydropyran-2-yloxy)-2-octyn-1-ol

Under an atmosphere of nitrogen, a solution of 5.6 g of propargyl alcohol in 30 ml of diethyl ether was added dropwise to a mixture of 5.06 g of lithium amide and 200 ml of liquid ammonia at −80° C., the mixture was stirred at −29° C. for 2 hours. To the solution was added dropwise a solution of 22.5 g of the pentane compound (prepared as described above) in 20 ml of diethyl ether at −29° C., the mixture was stirred at the same temperature for 5.5 hours. To the reaction mixture was added 2.7 g of ammonium chloride, and then the mixture was left overnight with stirring. To it was added water and diethyl ether, the aqueous layer was extracted with diethyl ether. The ethereal layer and the extract were combined, washed with a saturated aqueous solution of sodium chloride, dried over magnesium sulphate and concentrated under reduced pressure. The residue was purified by column chromatography on silica gel using a mixture of ethyl acetate and hexane (1:4) as eluent to give 4.2 g of the subtitle compound having the following physical characteristics:

TLC(benzene:ethyl acetate=4:1): Rf=0.32;

IR: $\nu$=3440, 2950, 2310, 2240, 1145, 1130, 1085, 1030 cm$^{-1}$.

NMR: $\delta$=4.5(1H,m), 4.2(2H,m), 4.0–3.1(4H,m), 2.4–2.0(3H,m), 2.0–1.3(12H,m).

MS(%): m/e=195(12.4), 125(8), 101(66.8), 85(100), 55(48.7).

(3) 8-(tetrahydropyran-2-yloxy)-1-methanesulphonyloxy-2-octyne

Under an atmosphere of nitrogen, a solution of 4.2 g of the octyn-1-ol compound (prepared as described above) in 10 ml of diethyl ether was added dropwise to 12.8 ml of an 1.45 M solution of butyl lithium in hexane at 0° C., the mixture was stirred at 0° C. for 30 minutes. To the solution was added dropwise a solution of 1.58 ml of methanesulphonyl chloride in 7 ml of diethyl ether, then stirred at 0° C. for 3 hours. The mixture was poured into cold water, extracted with diethyl ether, the extract was washed with a saturated aqueous solution of sodium chloride, dried over magnesium sulphate and concentrated under reduced pressure. The residue was purified by column chromatography on silica gel using a mixture of ethyl acetate and hexane (3:7) as eluent to give 4.1 g of the subtitle compound having the following physical characteristics:

TLC(benzene:ethyl acetate=4:1): Rf=0.51;

IR: $\nu$=2960, 2880, 2250, 1370, 1205, 1180, 1145, 1125, 1085, 1040, 1030, 980, 945, 815 cm$^{-1}$.

NMR: $\delta$=4.8(2H,t), 4.5(1H,m), 4.1–3.2(4H,m), 3.1(3H,s), 2.5–2.1(2H,m), 2.1–1.1(12H,m).

MS(%): m/e=125(8), 124(7.2), 107(27.2), 85(100), 79(34.8).

(4) 8-(tetrahydropyran-2-yloxy)-1-bromo-2-octyne

To a solution of 4.1 g of the methanesulphonyloxy compound (prepared as described above) in 50 ml of acetone was added 1.17 g of lithium bromide, the mixture was refluxed with heating for one hour. The reaction mixture was concentrated under reduced pressure, the residue was dissolved in diethyl ether, washed with water, a saturated aqueous solution of sodium chloride, dried over magnesium sulphate and concentrated under reduced pressure. The residue was purified by column chromatography on silica gel using a mixture of ethyl acetate and hexane (3:17) as eluent to give 3.42 g of the subtitle compound having the following physical characteristics:

TLC(ethyl acetate:hexane=3:17): Rf=0.45.

IR: $\nu$=2960, 2880, 2250, 1360, 1215, 1205, 1135, 1125, 1080, 1035, 1025, 910, 870, 815 cm$^{-1}$.

NMR: $\delta$=4.5(1H,m), 3.88(2H,t), 4.0–3.1(4H,m), 2.5–2.0(2H,m), 2.0–1.0(12H,m).

MS(%): m/e=209(17.8), 107(32.9), 101(52.9), 85(100), 79(39.1).

(5) 8-bromo-6-octyn-1-ol

To a solution of 3.42 g of the bromo compound (prepared as described above) in 34 ml of methanol was added 68 mg of p-toluenesulphonic acid, the mixture was stirred at 30°-40° C. for 2 hours. The reaction mixture was concentrated under reduced pressure, the residue was dissolved in diethyl ether, washed with a saturated aqueous solution of sodium bicarbonate, water, a saturated aqueous solution of sodium chloride, dried over magnesium sulphate and concentrated under reduced pressure. The residue was purified by column chromatography on silica gel using a mixture of ethyl acetate and hexane (3:17) as eluent to give 2.1 g of the subtitle compound having the following physical characteristics:

TLC(benzene:ethyl acetate=4:1): Rf=0.38.
IR: $\upsilon$=3350, 2950, 2875, 2250, 1220, 1050 cm$^{-1}$.
NMR: $\delta$=3.88(2H,t), 3.6(2H,t), 2.5-2.0(2H,m), 2.0-1.0(7H,m).
MS(%): m/e=125(32.5), 107(34.5), 91(60), 83(42.5), 79(100), 65(65.8), 55(76.5).

REFERENCE EXAMPLE 3

8-iodo-2-octynoic acid methyl ester

To a solution of 4.05 g of 8-bromo-2-octynoic acid methyl ester (prepared as described hereafter) in 24 ml of acetone was added 3.9 g of sodium iodide, the mixture was refluxed with heating for one hour, and concentrated under reduced pressure. The residue was dissolved in water, extracted with diethyl ether, the extract was washed with a saturated aqueous solution of sodium chloride, dried over sodium sulphate and concentrated under reduced pressure to give 4.80 g of the title compound having the following physical characteristics:

TLC(pentane:diethyl ether=3:1): Rf=0.42.
IR: $\upsilon$=2240, 1713, 1432, 1257, 1078, 756 cm$^{-1}$;
NMR: $\delta$=3.75(3H,s), 3.28(2H,t), 2.35(2H,m), 2.0-1.3(6H,m);
MS(%): m/e=280(M$^+$,4.7), 249(16), 248(12), 153(27), 121(24), 93(100).

8-bromo-2-octynoic acid methyl ester, used as a starting material in the above procedure, was prepared from propiolic acid and 1.5-dibromopentane as follows:

(1) 8-bromo-2-octynoic acid methyl ester

To a solution of 1.5 ml of diisopropylamine in 75 ml of tetrahydrofuran were added dropwise 135 ml of 1.5 M solution of butyl lithium in hexane, 75 ml of hexamethylphosphoramide (HMPA) and 6.15 ml of propiolic acid, successively, at −50° C., the mixture was allowed to heat to −10° C. over a period of 2 hours. To it was added dropwise 27.2 ml of 1,5-dibromopentane at −25° to −30° C., the solution allowed to heat to room temperature over a period of 2 hours, and stirred for one hour. The reaction mixture was poured into 500 ml of ice-water, extracted with methylene chloride, the extract washed with a saturated aqueous solution of sodium chloride, dried over sodium sulphate and concentrated under reduced pressure. The residue was dissolved in diethyl ether, there was added diazomethane-etherate until the solution was coloured pale yellow. After concentration under reduced pressure, the residue was purified by column chromatography on silica gel using chloroform as eluent to give 4.05 g of the subtitle compound having the following physical characteristics:

TLC(methylene chloride): Rf=0.57.
IR: $\upsilon$=2230, 1711, 1430, 1260, 1076, 752 cm$^{-1}$.
NMR: $\delta$=3.78(3H,s), 3.43(2H,t), 2.38(2H,m).
MS(%): m/e=203(48), 201(46), 121(57), 111(43), 93(100), 55(72).

REFERENCE EXAMPLE 4

(Z)-8-iodo-2-octenoic acid methyl ester

By the proceeding as described in Example 4 (described in hereafter) but utilizing 1.23 g of the octynoic acid methyl ester (prepared as described in Reference Example 3), there was obtained 0.88 g of the title compound having the following physical characteristics:

TLC(pentane:diethyl ether=3:1): Rf=0.54.
IR: $\upsilon$=1724, 1645 cm$^{-1}$.
NMR.$\delta$=6.23(1H,dt), 5.78(1H,d), 3.71(3H,t), 3.20(2H,t), 2.67(2H,m).
MS(%): m/e=282(M$^+$,16), 251(13), 155(100), 123(41), 113(55), 95(89).

REFERENCE EXAMPLE 5

(2RS)-8-bromo-2-methyloctanoic acid ethyl ester

By the proceeding as described in Reference Example 3(1) but utilizing 6.4 ml of 1,6-dibromohexane and 4.0 ml of propionic acid ethyl ester, there was obtained 3.02 g of the title compound having the following physical characteristics:

TLC(methylene chloride): Rf=0.49.
IR: $\upsilon$=1735, 1461, 1258, 1180 cm$^{-1}$.
NMR: $\delta$=4.14(2H,q), 3.40(2H,t), 2.40(1H,m), 1.86(2H,m), 1.29(3H,d), 1.18(3H,t).
MS(%): m/e=266(M$^+$,4), 264(M$^+$,4), 221(8), 219(7), 115(22), 102(100), 74(53), 69(38).

REFERENCE EXAMPLE 6

8-bromo-2,2-dimethyloctanoic acid ethyl ester

By the proceeding as described in Reference Example 3(1) but utilizing 1,6-dibromohexane and isobutyric acid ethyl ester, there was obtained the title compound having the following physical characteristics in 63% yields:

TLC(methylene chloride): Rf=0.52.
IR: $\upsilon$=1733, 1472, 1262, 1175, 1153, 1030 cm$^{-1}$.
NMR: $\delta$=4.13(2H,q), 3.41(2H,t), 1.84(1H,m), 1.24(3H,t), 1.16(6H,s).
MS(%): m/e=280(M+,1.8), 278(M+,1.9), 207(18), 205(19), 116(100), 88(27), 83(25), 69(50).

REFERENCE EXAMPLE 7

(2RS)-5-bromo-2-butylpentanoic acid ethyl ester

By the proceeding as described in Reference Example 3(1) but utilizing 1,3-dibromopropane and hexanoic acid ethyl ester, there was obtained the title compound having the following physical characteristics in 83% yields:

TLC(pentane:diethyl ether=3:1): Rf=0.54.
IR: $\upsilon$=1732, 1464, 1377, 1253, 1175, 1034 cm$^{-1}$.
NMR: $\delta$=4.16(2H,q), 3.41(2H,t), 2.34(2H,m), 1.27(3H,t), 0.90(3H,m).
MS(%): m/e=267(M$^+$,8), 265(M$^+$,9), 210(50), 209(50), 185(55), 111(26), 101(100), 73(31), 69(69).

REFERENCE EXAMPLE 8

8-bromo-3-methyloctanoic acid sec-butyl ester

A mixture of 337 mg of 3-methyl-8-(p-toluenesulphonyloxy)octanoic acid sec-butyl ester (prepared as described hereafter), 5 ml of acetone and 156 mg of lithium bromide was stirred at 70° C. for 1.5 hours. After evaporation under reduced pressure, the residue was dissolved in ethyl acetate, washed with water, a saturated aqueous solution of sodium chloride, dried over magnesium sulphate and concentrated under reduced pressure. The residue was purified by column chromatography on silica gel using a mixture of methylene chloride and cyclohexane (1:1) as eluent to give 204 mg of the title compound having the following physical characteristics:

TLC(benzene:ethyl acetate=8:1): Rf=0.80.

IR: $\nu$=2980, 2950, 2870, 1730, 1460, 1430, 1380, 1250, 1190, 1175, 1130, 1115, 1095 cm$^{-1}$.

NMR: $\delta$=5.10–4.30(1H,m), 3.56(1H,s), 3.30(1H,t).

MS(%): m/e=295(M+1,4.5), 293(M+1, 4.5), 239(31), 237(32), 221(53), 219(55), 213(11), 179(13), 178(13), 177(13), 176(12), 171(23), 157(50), 139(23), 117(14), 116(50), 111(23), 101(25), 97(39), 87(33), 75(19), 74(100), 73(23), 69(53), 61(17), 60(55), 59(12), 57(67), 56(86), 55(62), 43(30), 42(17), 41(67).

3-methyl-8-(p-toluenesulphonyloxy)octanoic acid sec-butyl ester, used as a starting material in the above procedure, was prepared from 5-bromo-1-(tetrahydropyran-2-yloxy)pentane and crotonic acid sec-butyl ester as follows:

(1) 3-methyl-8-(tetrahydropyran-2-yloxy)octanoic acid sec-butyl ester

Under an atmosphere of nitrogen, a mixture of 250 mg of magnesium, 2.8 g of 5-bromo-1-(tetrahydropyran-2-yloxy)pentane, 200 μl of ethyl bromide, a trace amount of iodine and 4 ml of tetrahydrofuran was refluxed with heating for one hour. To it were added 516 mg of crotonic acid sec-butyl ester and 14 mg of cuprous chloride at 0° C. over a period of 30 minutes, the mixture stirred at 0° C. for 15 minutes, and then at room temperature for one hour. The reaction mixture was poured into a saturated aqueous solution of ammonium chloride, extracted with ethyl acetate, the extract washed with a saturated aqueous solution of sodium chloride, dried over magnesium sulphate and concentrated under reduced pressure. The residue was purified by column chromatography on silica gel using a mixture of methylene chloride and ethyl acetate (20:1) as eluent to give 529 mg of the subtitle compound having the following physical characteristics:

TLC(chloroform): Rf=0.15.

IR: $\nu$=2950, 2870, 1735, 1460, 1380, 1355, 1260, 1200, 1120, 1080, 1030 cm$^{-1}$.

NMR: $\delta$=5.15–4.20(2H,m), 4.20–2.90(4H,m).

(2) 3-methyl-8-(p-toluenesulphonyloxy)octanoic acid sec-butyl ester

To a solution of 529 mg of the tetrahydropyran-2-yloxy compound (prepared as described above) in 0.8 ml of tetrahydrofuran was added 8 ml of 65% aqueous acetic acid, the mixture stirred at 80°–85° C. for 30 minutes, and neutralized with sodium bicarbonate. After evaporation under reduced pressure, the residue was dissolved in ethyl acetate, filtered, and the filtrate dried over magnesium sulphate and concentrated under reduced pressure to give oily 8-hydroxy-3-methyloctanoic acid sec-butyl ester.

A mixture of the oily ester, thus obtained, one ml of pyridine and 485 mg of p-toluenesulphonyl chloride was stirred at room temperature for 16 hours. The reaction mixture was poured into ice-water, extracted with ethyl acetate, the extract washed with dilute sulphuric acid, a saturated aqueous solution of sodium bicarbonate, a saturated aqueous solution of sodium chloride, dried over magnesium sulphate and concentrated under reduced pressure. The residue was purified by column chromatography on silica gel using a mixture of methylene chloride and ethyl acetate (20:1) as eluent to give 647 mg of the subtitle compound having the following physical characteristics:

TLC(benzene:ethyl acetate=2:1): Rf=0.83;

IR: $\nu$=2980, 2950, 2860, 1730, 1600, 1460, 1360, 1190, 1180, 1095 cm$^{-1}$.

NMR: $\delta$=7.40(4H,m), 4.71(1H,m), 3.98(2H,t), 2.36(3H,s).

MS(%): m/e=384(M$^+$,13), 342(12), .312(21), 311(64), 310(85), 296(13), 173(33), 157(21), 155(26), 139(54), 111(44), 97(100), 96(56), 91(54), 69(54).

REFERENCE EXAMPLE 9

(E)-1-(3-ethoxycarbonyl-1,1-dimethyl-2-propenyl)imidazole

A mixture of 0.75 g of 1-(1-formyl-1-methylethyl)imidazole (prepared as described hereafter), 1.80 g of ethoxycarbonylmethylidenetriphenylphosphorane and 9 ml of chloroform was stirred overnight at room temperature. After evaporation under reduced pressure, the residue was purified by column chromatography on silica gel using a mixture of chloroform and ethanol (49:1) as eluent to give 0.79 g of the title compound having the following physical characteristics:

TLC(chloroform:methanol=10:1): Rf=0.40.

IR: $\nu$=1720, 1657, 1314, 1186, 1036, 664 cm$^{-1}$.

NMR: $\delta$=7.59(1H,m), 7.08(1H,m), 7.02(1H,dt), 6.92(1H,m), 5.6(1H,d), 4.18(2H,q), 1.92(6H,s), 1.28(3H,t).

MS(%): m/e=208(M$^+$,50), 141(54), 135(100), 113(64), 95(60), 67(46).

1-(1-formyl-1-methylethyl)imidazole, used as a starting material in the above procedure, was prepared from 1-(1-ethoxycarbonyl-1-methylethyl)imidazole [prepared as described in Example 2(5)] as follows:

(1) 1-(1-formyl-1-methylethyl)imidazole

By the proceeding as described in Reference Example 1 but utilizing 1-(1-ethoxycarbonyl-1-methylethyl)imidazole, there was obtained the subtitle compound having the following physical characteristics in 77% yields:

TLC(chloroform:methanol=10:1): Rf=0.12.

MS(%): m/e=138(M$^+$,30), 109(100), 82(52).

REFERENCE EXAMPLE 10

1-[(4E,6E)-7-ethoxycarbonyl-1,1-dimethyl-4,6-heptadienyl]imidazole

Under an atmosphere of nitrogen, 2.0 g of diethyl (E)-3-ethoxycarbonyl-2-propenylphosphonate was added dropwise to 25 ml of a 0.32 M solution of lithium diisopropylamide in tetrahydrofuran at −78° C. and the mixture was stirred at −70° C. for 30 minutes. To it was added a solution of 1.0 g of 1-(3-formyl-1,1-dimethylpropyl)imidazole (prepared as described hereafter) in 2 ml of tetrahydrofuran at −70° C., the mixture was stirred at room temperature for 30 minutes. To it was added 0.91 ml of acetic acid. After evaporation under reduced pressure, the residue was dissolved in chloroform, washed with a saturated aqueous solution of sodium bicarbonate, water, dried over sodium sulphate and concentrated under reduced pressure. The residue was purified by column chromatography on silica gel using a mixture of chloroform and ethanol (99:1) as eluent to give 0.85 g of the title compound having the following physical characteristics:

TLC(chloroform:methanol=10:1): Rf=0.45.

IR: $\upsilon$=3400, 3110, 1710, 1640, 1617, 1486, 1252, 1144, 1008, 666 cm$^{-1}$.

NMR: $\delta$=7.6(1H,m), 7.09(1H,m), 7.03(1H,m), 7.4–7.0(1H,m), 6.3–5.9(2H,m), 5.79(1H,d), 4.20(2H,q), 1.9(4H,m), 1.57(6H,s), 1.27(3H,t).

MS(%): m/e=262(M+,34), 261(26), 233(33), 217(22), 189(48), 149(100), 119(22), 69(39), 67(27).

1-(3-formyl-1,1-dimethylpropyl)imidazole, used as a starting material in the above procedure, was prepared from 1-(3-ethoxycarbonyl-1,1-dimethylpropyl)imidazole (prepared as described in Example 5) as follows:

(1) 1-(3-formyl-1,1-dimethylpropyl)imidzole

By the proceeding as described in Reference Example 1 but utilizing 1-(3-ethoxycarbonyl-1,1-dimethylpropyl)imidazole, there was obtained the sutitle compound having the following physical characteristics in 76% yields:

TLC(chloroform:ethanol=5:1): Rf=0.41.

IR: $\upsilon$=3130, 1723, 1490, 1379, 1241, 1087, 1009, 667 cm$^{-1}$.

NMR: $\delta$=9.5(1H,bs), 7.5(1H,m), 7.0(2H,m), 2.2(4H,m), 1.6(6H,s).

MS(%): m/e=166(M+,55), 138(39), 81(91), 69(100), 68(50).

REFERENCE EXAMPLE 11

1-(4-chlorobutyl)imidazole

By the proceeding as described in Example 2 but utilizing 1,4-dichlorobutane, there was obtained the title compound having the following physical characteristics in 40% yields:

TLC(chloroform:methanol=9:1): Rf=0.30.

IR: $\upsilon$=3400, 3110, 2950, 1675, 1510, 1450, 1235, 1110, 1080 cm$^{-1}$.

NMR: $\delta$=7.2(1H,s), 7.0–6.6(2H,d), 4.2–3.7(2H,t), 3.7–3.2(2H,t), 2.3–1.3(4H,m).

MS(%): m/e=158(M+,50), 123(100), 96(18.7), 82(21.8), 81(75), 69(62.5), 68(34), 55(56), 54(40.6).

REFERENCE EXAMPLE 12

(E)-1-(7-methoxycarbonyl-5,5-dimethyl-6-heptenyl)imidazole

By the proceeding as described in Example 1 but utilizing 1-(5-formyl-5-methylhexyl)imidazole and diethyl methoxycarbonylmethylphosphonate, there was obtained the title compound having the following physical characteristic in 66% yields:

TLC(chloroform:methanol=9:1): Rf=0.52.

1-(5-formyl-5-methylhexyl)imidazole, used as a starting material in the above procedure, was prepared from 1-(5-ethoxycarbonyl-5-methylhexyl)imidazole (prepared as described in Example 6) as follows:

(1) 1-(5-formyl-5-methylhexyl)imidazole

By the proceeding as described in Reference Example 1 but utilizing 1-(5-ethoxycarbonyl-5-methylhexyl)imidazole, there was obtained the subtitle compound having the following physical characteristics in 40% yields:

TLC(chloroform:methanol)=9:1): Rf=0.25.

IR: $\upsilon$=3700–3200, 2950, 1730, 1510, 1240 cm$^{-1}$.

NMR: $\delta$=9.2(1H,s), 7.5(1H,s), 7.1–6.7(2H,d), 4.2–3.7(2H,t).

MS(%): m/e=194(M,20), 166(76), 139(42), 123(38), 110(18), 96(30), 82(100), 81(50), 69(70).

REFERENCE EXAMPLE 13

1-[(1RS,3E,5E)-6-methoxycarbonyl-1-methyl-3,5-hexadienyl]imidazole

A mixture of 0.68 g of imidazole, 0.82 ml of crotonaldehyde and 8 ml of acetonitrile was stirred overnight at room temperature. To it were added 20 ml of acetonitrile and 3.6 g of (E)-3-methoxycarbonyl-2-propenylidenetriphenylphosphorane, and the mixture was stirred at ambient temperature for 1.5 hours. After concentration under reduced pressure, the residue was purified by column chromatography on silica gel using a mixture of chloroform and methanol (97:3) as eluent to give 0.71 g of the title compound having the following physical characteristics:

MS(%): m/e=220(M+,38), 161(32), 121(42), 95(100).

REFERENCE EXAMPLE 14

1-[(2RS,3E,5E)-6-methoxycarbonyl-2-methyl-3,5-hexadienyl]imidazole

By the proceeding as described in Reference Example 13 but utilizing methacrolein, there was obtained the title compound having the following physical characteristic in 41% yields:

MS(%): m/e=220(M+,42), 161(36), 81(100), 79(47).

EXAMPLE 1

(E)-1-(7-ethoxycarbonyl-6-heptenyl)imidazole

Under an atmosphere of nitrogen, 780 mg of diethyl ethoxycarbonylmethylphosphonate was added dropwise to a suspension of 120 mg of sodium hydride (content 63.5%) in 20 ml of tetrahydrofuran at room temperature, and the mixture was stirred at ambient temperature for about 15 minutes. To it was added dropwise a solution of 480 mg of the formyl compound (prepared as described in Reference Example 1) in 5 ml of tetrahydrofuran, and the mixture was stirred at room temperature for one hour. The reaction mixture was quenched by a saturated aqueous solution of ammonium chloride, and when evaporated under reduced pressure. The residue was dissolved in ethyl acetate, washed with a saturated aqueous solution of sodium bicarbonate, a saturated aqueous solution of sodium chloride, dried over magnesium sulphate and concentrated under reduced pressure. The residue was purified by column chromatography on silica gel using a mixture of chloroform and methanol (100:3) as eluent to give 540 mg of the title compound having the following physical characteristics:

TLC(chloroform:methanol)=10:1): Rf=0.35.

IR: $\upsilon$=3130, 2950, 1720, 1655, 1505, 1345, 1270, 1230, 1187, 1040 cm$^{-1}$.

NMR: δ=7.33(1H,s), 6.91(1H,m), 6.78(1H,dt), 6.74(1H,m), 5.71(1H,dt), 4.16(2H,q), 3.84(2H,t).

MS(%): m/e=236(M+,20), 191(24), 123(30), 110(30), 109(30), 82(100), 81(50), 69(42), 55(30).

EXAMPLE 2

1-(7-methoxycarbonyl-2-heptynyl)imidazole

Under an atmosphere of nitrogen, 501 mg of imidazole was added to a suspension of 280 mg of sodium hydride (content 63.5%) in 20 ml of N,N-dimethylformamide, the mixture was stirred at 110° C. for 15 minutes. To it was added dropwise a solution of 1.55 g of the ester (prepared as described in Reference Example 2) in one ml of N,N-dimethylformamide at 110° C., and then the mixture was stirred at the same temperature for 50 minutes. The reaction mixture was evaporated under reduced pressure, the residue was dissolved in diethyl ether, washed with water, dried over magnesium sulphate and concentrated under reduced pressure. The residue was purified by column chromatography on silica gel using chloroform as eluent to give 475 mg of the title compound having the following physical characteristics:

TLC(chloroform:methanol=9:1): Rf=0.48.

IR: υ=3130, 2970, 2880, 2250, 1740, 1510, 1440, 1235, 1180, 1160, 1110, 1080, 910, 825, 740 cm⁻¹.

NMR: δ=7.59(1H,m), 7.07(1H,m), 7.03(1H,m), 4.7(2H,t), 3.68(3H,s), 2.5-2.1(4H,m), 1.95-1.4(4H,m).

MS(%): m/e=220(M+,68.9), 219(31.1), 189(45.4), 161(30.3), 133(35.3), 119(44.5), 79(40.3), 77(39.5), 69(100).

The following compounds were prepared by the same procedure as described above.

(1) 1-[(7RS)-7-ethoxycarbonyloctyl]imidazole

The compound, having the following physical characteristics, was prepared from (2RS)-8-bromo-2-methyloctanoic acid ethyl ester (prepared as described in Reference Example 5); and the additional purification was carried out by distillation in vacuo.

Boiling point: 167°-173° C./0.2 mmHg;

TLC (chloroform:methanol=10:1): Rf=0.36.

IR: υ=3110, 2945, 1731, 1507, 1233, 1185, 1092, 667 cm⁻¹.

NMR: δ=7.45 (1H, m), 7.05 l (1H, m), 6.90 (1H, m), 4.13 (2H, q), 3.92 (2H, t), 2.40 (1H, m), 1.24 (3H, t), 1.13 (3H, d).

MS(%): m/e=252(M+, 17), 251(100), 207(57), 151(70), 82(88), 69(50).

(2) 1-(7-ethoxycarbonyl-7-methyloctyl)imidazole

The compound, having the following physical characteristics, was prepared from 8-bromo-2,2-dimethyloctanoic acid ethyl ester (prepared as described in Reference Example 6), and the additional purification was carried out by distillation in vacuo.

Boiling point: 156°-157° C./0.1 mmHg.

TLC (chloroform:methanol=10.1): Rf=0.36.

IR: υ=3110, 2940, 1727, 1503, 1219, 1173, 1169, 907, 663 cm⁻¹.

NMR δ=7.46 (1H, m), 7.05 (1H, m), 6.90 (1H, m), 4.11 (2H, q), 3.92 (2H, t), 1.23 (3H, t), 1.12 (6H, s).

MS(%): m/e=266(M+,46), 265(100), 193(57), 151(81), 69(55).

(3) 1-[(4RS)-4-ethoxycarbonyloctyl]imidazole

The compound, having the following physical characteristics, was prepared from (2RS)-5-bromo-2-butylpentanoic acid ethyl ester (prepared as described in Reference Example 7).

TLC (chloroform:methanol=10:1): Rf=0.35.

IR: υ=3105, 2930, 1729, 1505, 1462, 1379, 1129, 1180, 1154, 1111, 1090, 1038, 910, 667 cm⁻¹.

NMR: δ=7.44 (1H, m), 7.05 (1H, m), 6.89 (1H, m), 4.13 (2H, q), 3.94 (2H, t), 2.33 (1H, m), 1.26 (3H, t), 0.89 (3H, m).

MS(%): m/e=252(M+,55), 209(100), 207(25), 179(56), 109(29), 96(93), 95(48), 82(51), 81(24), 69(28).

(4) 1-[(6RS)-7-sec-butoxycarbonyl-6-methylheptyl]imidazole

The compund, having the following physical characteristics, was prepared from 8-bromo-3-methyloctanoic acid sec-butyl ester (prepared as described in Reference Example 8).

TLC (chloroform:methanol=9:1): Rf=0.35.

IR: υ=3400, 2970, 2945, 2860, 1730, 1510, 1460, 1380, 1235, 1110, 1095, 1080, 1030, 985 cm⁻¹.

NMR: δ=7.50-6.98 (1H, m), 6.98-6.32 (2H, m), 5.10-4.45 (1H, m), 3.80 (2H, t), 3.51 (1H, s).

MS(%): m/e=280(M+,35), 279(45), 238(20), 237(36), 223(16), 208(18), 207(100), 206(14), 185(12), 180(26), 179(28), 166(12), 165(58), 138(20), 137(44), 124(24), 123(44), 110(14), 109(24), 97(20), 96(32), 95(38), 83(20), 82(70), 81(34), 69(52), 68(18), 57(26), 56(16), 55(44), 54(14), 43(18), 41(42).

(5) 1-(1-ethoxycarbonyl-1-methylethyl)imidazle

The compound, having the following physical characteristics, was prepared from 2-bromo-2-methylpropanoic acid ethyl ester.

TLC (chloroform:methanol=10:1): Rf=0.35.

IR: υ=3110, 2985, 1740, 1490, 1273, 1241, 1175, 1142, 1091, 1020, 1007, 907, 752, 661 cm⁻¹.

NMR: δ=7.6 (1H, m), 7.0 (2H, m), 4.2 (2H, q), 1.8 (6H, s), 1.2 (3H, t).

MS(%): m/e=183(30), 182(M+,100), 109886), 82(50).

EXAMPLE 3

1-(7-methoxycarbonyl-6-heptynyl)imidazole

To a solution of 3.63 g of the iodo compound (prepared as described in Reference Example 3) in 70 ml of toluene was added 6.8 g of imidazole silver salt (prepared as described hereafter), and the mixture was refluxed with heating for 20 minutes. The reaction mixture was filtered, and the filtrate was concentrated under reduced pressure. The residue was purified by column chromatography on silica gel using a mixture of methanol and chloroform (3:97) as eluant to give 0.214 g of the title compound having the following physical characteristics:

TLC (chloroform:methanol=10.1): Rf=0.33.

IR: υ=2240, 1712, 1432, 1263, 1078, 756, 667 cm⁻¹.

NMR: δ=7.47 (1H, m), 7.05 (1H, m), 6.91 (1H, m), 3.96 (2H, t), 3.77 (3H, s), 2.34 (2H, t).

MS(%): m/e=220(M+,39), 189(42), 161(31), 123(26), 82(100), 81(52).

The following compound was prepared by the same procedure as described above.

(1) (Z)-1-(7-methoxycarbonyl-6-heptenyl)imidazole

The compound, having the following physical characteristics, was prepared from the octenoic acid methyl ester compound (prepared as described in Reference Example 4).

TLC (chloroform:methanol=10:1): Rf=0.39.

IR: υ=3110, 1722, 1643, 1506, 1437, 1196, 1173, 820, 665 cm⁻¹.

NMR: δ=7.47(1H, m), 7.06(1H, m), 6.92(1H, m), 6.21(1H, dt), 5.79(1H, d), 3.95(2H, t), 3.71(3H, s).

MS(%): m/e=222(M⁺, 24), 110(25), 109(24), 82(100), 81(29), 79(30).

Imidazole silver salt, used in the above procedure, was obtained as follows.

To a solution of 16.9 g of silver nitrate in 680 ml of water were added a solution of 6.8 g of imidazole in 280 ml of water at room temperature, and a solution of 4.3 g of sodium hydroxide in 20 ml of water at 90° C. The mixture was allowed to cool to 50° C., and stirred at that temperature for 6 hours. The reaction mixture was filtered, the solid washed with cold water, ethanol, acetone, diethyl ether, successively, and dried under vacuum to give 24 g of the desired imidazole salt.

EXAMPLE 4

(Z)-1-(7-methoxycarbonyl-2-hetpenyl)imidazole

To a solution of 220 mg of the 2-heptynyl compound (prepared as described in Example 2) in 6 ml of methanol were added 15 mg of quinoline and 16 mg of 5% palladium on barium sulphate. The hydrogenation of the compound was stopped with uptake of 23 ml of hydrogen. The reaction mixture was filtered, and the filtrate was evaporated under reduced pressure. The residue was purified by column chromatography on silica gel using chloroform as eluent to give 192 mg of the title compound having the following physical characteristics:

TLC (chloroform:methanol=9:1): Rf=0.48.

IR:υ=3125, 3045, 2960, 2880, 1740, 1510, 1440, 1240, 1180, 1160, 1115, 1085, 1040, 915 cm⁻¹.

NMR: δ=7.48(1H, m), 7.05(1H, m), 6.91(1H, m), 5.9-5.4(2H, m), 4.57(2H, d), 3.68(3H, s), 2.5-2.0(4H, m), 1.9-1.2(4H, m).

MS(%): m/e=222(38.5), 191(34), 154(31), 81(49.5), 80(71), 69(100).

EXAMPLE 5

1-(3-ethoxycarbonyl-1,1-dimethylpropyl)imidazole

A mixture of 0.59 g of the 2-propenyl compound (prepared as described in Reference Example 9), 0.30 g of 5% palladium on carbon and 6 ml of ethanol was stirred at room temperature for 1.5 hours under an atmosphere of hydrogen, and the catalyst was filtered off. After evaporation under reduced pressure, the residue was purified by column chromatography on silica gel using a mixture of chloroform and ethanol (99:1) as eluent to give 0.57 g of the title compound having the following physical characteristics:

TLC (chloroform:methanol=10:1): Rf=0.34.

IR: υ=3110, 1733, 1488, 1377, 1300, 1242, 1184, 1083, 908, 663 cm⁻¹.

NMR: δ=7.5(1H, m), 6.98(1H, m), 6.9(1H, m), 4.03(2H, q), 2.07(4H, bs), 1.87(6H, s), 1.20(3H, t).

MS(%): m/e=210(M⁺,45), 166(55), 143(47), 97(86), 69(100).

The following compounds were prepared by the same procedure as described above.

(1) 1-(7-ethoxycarbonyl-1,1-dimethylheptyl)imidazole

The compound, having the following physical characteristics, was prepared from the heptadienyl compound (prepared as described in Reference Example 10).

TLC (chloroform:methanol=10:1): Rf=0.45.

IR: υ=3400, 1732, 1488, 1375, 1234, 1178, 1084, 1033, 668 cm⁻¹.

NMR: δ=7.59(1H, m), 7.06(1H, m), 7.01(1H, m), 4.12(2H, q), 2.26(2H, t), 1.52(6H, s), 1.23(3H, t).

MS(%): m/e=266(M⁺,16), 265(28), 221(15), 110(21), 109(18), 69(100).

(2) 1-(7-methoxycarbonyl-5,5-dimethylheptyl)imidazole

The compound, having the following physical characteristics, was prepared from the heptenyl compound (prepared as described in Reference Example 12).

IR: υ=3600-3200, 2950, 1740, 1510, 1440, 1370 cm⁻¹.

NMR: δ=7.7(1H, s), 7.1-6.6(2H, d), 4.3-3.8(2H, t), 3.6(3H, s).

MS(%): m/e=252(M⁺,65), 251(88), 237(35), 221(41), 183(29), 165(76), 149(29), 123(94), 96(47), 95(41), 82(82), 81(35), 69(100).

(3) 1-[(1RS)-6-methoxycarbonyl-1-methylhexyl]imidazole

The compound, having the following physical characteristics, was prepared from the hexadienyl compound (prepared as described in Reference Example 13).

TLC (chloroform:methanol=10:1): Rf=0.29.

IR: υ=3105, 2940, 1738, 1496, 1437, 1228, 1111, 1077, 910, 668 cm⁻¹.

NMR: δ=7.49(1H, m), 7.05(1H, m), 6.93(1H, m), 4.15(1H, m), 3.68(3H, s), 2.28(2H, t), 1.49(3H, d).

MS(%): m/e=224(M⁺,43), 223(100), 193(28), 96(56), 95(46), 69(45).

(4) 1-[(2RS)-6-methoxycarbonyl-2-methylhexyl]imidazole

The compound, having the following physical characteristics, was prepared from the hexadienyl compound (prepared as described in Reference Example 14).

TLC (chloroform:methanol=10:1): Rf=0.20;

IR: υ=3105, 2930, 1737, 1506, 1435, 1233, 1108, 1077, 909, 732, 663 cm⁻¹.

NMR: δ=7.42(1H, m), 7.04(1H, m), 6.88(1H, m), 4.0-3.5(2H, m), 3.69(3H, s), 2.33(2H, t), 0.96(3H, d).

MS(%): m/e=224(M⁺,37), 223(100), 193(24), 82(69), 81(31), 69(28).

EXAMPLE 6

1-(5-ethoxycarbonyl-5-methylhexyl)imidazole

Under an atmosphere of nitrogen, 8.65 ml of a 1.5 M solution of butyl lithium in hexane was added dropwise to a solution of 1.85 ml of diisopropylamine in 20 ml of tetrahydrofuran at −70° C., and the mixture was stirred at that temperature for 15 minutes. To it was added dropwise a solution of 1.862 ml of isobutyric acid ethyl ester in 3 ml of tetrahydrofuran, and the mixture was stirred at −70° C. for 30 minutes. The solution, thus obtained, was added dropwise to a solution of 2 g of the chlorobutyl compound (prepared as described in Reference Example 11) in 20 ml of tetrahydrofuran at −70° C. over a period of 40 minutes and the mixture was stirred at that temperature for one hour. After evaporation under reduced pressure, the residue was quenched with 1.0 N hydrochloric acid, extracted with ethyl acetate, the extract was washed with a saturated aqueous solution of sodium chloride, dried over magnesium sulphate and concentrated under reduced pressure. The residue was purified by column chromatography on silica gel using chloroform as eluent to give 2.1 g of the title compound having the following physical characteristics:

IR: $\upsilon$=3000, 2950, 1720, 1500, 1470, 1450, 1390, 1230, 1180 cm$^{-1}$.

NMR: $\delta$=7.4(1H,s), 7.15–6.70(2H,d), 4.5–3.2(4H,m).

MS(%): m/e=238(M$^+$,19), 237(24), 165(43), 123(100), 109(14), 95(43), 82(48), 81(71), 69(57).

EXAMPLE 7

(E)-1-(7-carboxy-6-heptenyl)imidazole hydrochloride

To 140 mg of the ester compound (prepared as described in Example 1) was added 0.9 ml of 2 N aqueous sodium hydroxide, and the mixture was stirred at ambient temperature for one hour. The reaction mixture was washed with diethyl ether, acidified with 6 N hydrochloric acid at pH 1, and then evaporated under reduced pressure. To the residue was added 3 ml of tert-butanol, and evaporated under reduced pressure. The residue was dissolved in ethanol, an insoluble material was filtered off, and then the filtrate was concentrated under reduced pressure, and these operations were carried out once again. The residue was purified by crystallization with a mixture of ethanol and diethyl ether to give 71 mg of the title compound having the following physical characteristics:

Melting point: 144°–146° C.

TLC (ethyl acetate:acetic acid:water=3:1:1): Rf=0.44.

IR (Kbr tablet): $\upsilon$=3130, 1700, 1650, 1580, 1542, 1262, 1220, 1190, 820 cm$^{-1}$.

NMR (dimethyl sulphoxide-d solution): $\delta$=9.28(1H, m), 7.86(1H, m), 7.72(1H, m), 6.85(1H, dt), 5.92(1H, dt), 4.26(2H, t).

MS(%): m/e=208(M$^+$,13), 110(23), 109(22), 96(24), 95(23), 82(100), 81(50), 69(37), 68(22), 55(50).

The following compounds were prepared by the same procedure as described above.

(1) 1-(7-carboxy-2-heptynyl)imidazole hydrochloride

The compound, having the following physical characteristics, was prepared from the ester compound (prepared as described in Example 2).

Melting point: 137°–139° C.

IR (KBr tablet): $\upsilon$=3400, 3175, 3130, 3050, 3010, 2970, 2850, 2250, 1730, 1585, 1540, 1410, 1290, 1245, 1185, 1085, 845, 785, 630 cm$^{-1}$.

NMR (D$_2$O solution): $\delta$=8.87(1H, m), 7.64(1H, m), 7.54(1H, m), 5.10(2H, t), 4.76(1H, s), 2.6–2.1(4H, m), 2.0–1.3(4H, m).

MS(%): m/e=206(5.9), 151(6.5), 119(20.9), 79(24.8), 77(21.6), 69(100).

(2) (Z)-1-(7-carboxy-2-heptenyl)imidazole hydrochloride

The compound, having the following physical characteristics, was prepared from the ester compound (prepared as described in Example 4).

Melting point: 81°–83° C.

TLC (ethyl acetate:acetic acid:water=3:1:1): Rf=0.58.

IR (KBr tablet): $\upsilon$=3420, 3150, 3050, 2950, 2870, 1720, 1580, 1550, 1400, 1290, 1090, 640 cm$^{-1}$.

NMR (D$_2$O solution): $\delta$=8.73(1H, m), 7.51(2H, m), 6.20–5.00(2H, m), 4.93(2H, d), 4.75(1H, 's), 2.6–2.0(4H, m), 2.0–1.1(4H, m).

MS(%): m/e=208(8.6), 140(19.5), 121(9.8), 81(48.9), 80(57.5), 69(100).

(3) 1-(7-carboxy-6-heptynyl)imidazole hydrochloride

The compound, having the following physical characteristics, was prepared from the ester compound (prepared as described in Example 3).

Melting point: 92°–95° C.

IR (KBr tablet): $\upsilon$=3370, 3130, 3060, 2955, 2240, 1702, 1628, 1540, 1256, 1083, 758, 640 cm$^{-1}$.

NMR (D$_2$O solution): $\delta$=8.79(1H, m), 7.57(1H, m), 7.53(1H, m), 4.3(2H, t), 2.44(2H, t), 2.2–1.1(6H, m).

MS(%): m/e=189(M-18,2), 162(32), 161(23), 121(24), 82(51), 81(56), 55(42), 44(100).

(4) (Z)-1-(7-carboxy-6-heptenyl)imidazole hydrochloride

The compound, having the following physical characteristics, was prepared from the ester compound [prepared as described in Example 3(1)].

IR: $\upsilon$=3600–3200, 1716, 1641, 1575, 1546, 1462, 1178, 1087 cm$^{-1}$.

NMR (D$_2$O solution): $\delta$=8.73(1H, m), 7.50(2H, m), 6.35(1H, dt), 5.84(1H, d), 4.26(2H, t), 2.57(2H, m), 1.93(2H, m).

MS(%): m/e=208(M$^+$,19), 123(19), 110(26), 109(26), 96(22), 95(15), 82(100), 81(37).

(5) 1-[(7RS)-7-carboxyoctyl]imidazole hydrochloride

The compound, having the following physical characteristics, was prepared from the ester compound [prepared as described in Example 2(1)].

IR: $\upsilon$=3600–2300, 1722, 1576, 1545, 1460, 1188, 1087 cm$^{-1}$.

NMR (D$_2$O solution): $\delta$=8.78(1H, m), 7.53(2H, m), 4.28(2H, t), 2.50(1H, m), 1.15(3H, d).

MS(%): m/e=224(M$^+$,10), 223(29), 180(23), 151(36), 123(23), 96(33), 95(28), 82(100), 81(35).

(6) 1-(7-carboxy-7-methyloctyl)imidazole hydrochloride

The compound, having the following physical characteristics, was prepared from the ester compound [prepared as described in Example 2(2)].

IR: $\upsilon$=3600–2300, 1718, 1578, 1546, 1472, 1171, 1087 cm$^{-1}$.

NMR (D$_2$O solution): $\delta$=8.90(1H, m), 7.56(2H, m), 4.29(2H, t), 1.18(6H, s).

MS(%): m/e=237(M$^+$-1,33), 194(37), 151(70), 96(42), 82(100).

(7) 1-[(4RS)-4-carboxyoctyl]imidazole hydrochloride

The compound, having the following physical characteristics, was prepared from the ester compound [prepared as described in Example 2(3)].

IR: $\upsilon$=3600–2300, 1724, 1575, 1546, 1452, 1288, 1190, 1087 cm$^{-1}$.

NMR (D$_2$O solution): $\delta$=8.82(1H, m), 7.57(2H, m), 4.32(2H, t), 2.46(1H, m), 1.95(2H, m), 0.88(3H, m).

MS(%): m/e=224(M$^+$,27), 181(100), 96(76), 95(28), 82(68), 81(39), 69(54), 68(31).

(8) 1-[(6RS)-7-carboxy-6-methylheptyl]imidazole hydrochloride

The compound, having the following physical characteristics, was prepared from the ester compound [prepared as described in Example 2(4)].

TLC (ethyl acetate:water:acetic acid=3:1:1): Rf=0.60.

IR: $\nu$=3360, 3140, 2970, 2940, 2860, 2615, 1720, 1580, 1550, 1460, 1385, 1290, 1185, 1085, 1040 cm$^{-1}$.

NMR (D$_2$O solution): $\delta$=8.90–8.50(1H, m), 7.90–7.10(2H, m), 4.25(2H, t), 0.94(3H, d).

MS(%): m/e=224(M+,19), 223(45), 197(16), 180(24), 179(21), 165(36), 149(11), 138(11), 137(30), 124(19), 123(33), 109(19), 97(16), 96(32), 95(27), 83(21), 82(100), 81(40), 69(36), 68(22), 67(11), 55(40), 54(13), 41(30).

(9) 1-(3-carboxy-1,1-dimethylpropyl)imidazole hydrochloride

The compound, having the following physical characteristics, was prepared from the ester compound (prepared as described in Example 5).

Melting point: 126°–127° C.

IR (KBr tablet): $\nu$=3400, 3130, 2990, 1722, 1573, 1402, 1383, 1195, 1087, 662, 621 cm$^{-1}$.

NMR (D$_2$O solution): $\delta$=8.91(1H, m), 7.77(1H, m), 7.61(1H, m), 2.33(4H, bs), 1.73(6H, s).

MS(%): m/e=182(M+,27), 97(33), 73(19), 69(100), 68(95).

(10) 1-(7-carboxy-1,1-dimethylheptyl)imidazole hydrochloride

The compound, having the following physical characteristics, was prepared from the ester compound [prepared as described in Example 5(1)].

Melting point: 140°–141° C.;

IR (KBr tablet): $\nu$=3400, 3120, 1720, 1573, 1382, 1250, 1088, 666 cm$^{-1}$.

NMR (D$_2$O solution): $\delta$=8.84(1H,m), 7.73(1H, m), 7.58(1H, m), 2.38(2H, t), 1.92(2H, m), 1.68(6H, s).

MS(%): m/e=238(M+,8), 237(11), 223(15), 110(23), 109(19), 83(13), 69(100), 68(20).

(11) 1-(7-carboxy-5,5-dimethylheptyl)imidazole hydrochloride

The compound, having the following phydical characteristics, was prepared from the ester compound [prepared as described in Example 5(2)].

IR: $\nu$=3600–2500, 1720, 1580, 1550, 1460 cm$^{-1}$.

NMR: (D$_2$O solution) $\delta$=8.72(1H, s), 7.6–7.4(2H, m), 4.4–4.1(2H, t).

MS(%): m/e=238(M,9.5), 237(21), 194(11), 166(17), 165(41), 123(100), 110(13), 96(33), 95(22), 82(71), 81(31), 69(59).

(12) 1-[(1RS)-6-carboxy-1-methylhexyl]imidazole hydrochloride

The compound, having the following physical characteristics, was prepared from the ester compound [prepared as described in Example 5(3)].

Melting point: 116° C.–119° C.

IR (KBr tablet): $\nu$=3410, 3130, 2940, 2860, 1720, 1636, 1571, 1540, 1387, 1295, 1190, 1096, 768, 626 cm$^{-1}$.

NMR (D$_2$O solution): $\delta$=8.76(1H,m), 7.58(1H,m), 7.49(1H,m), 4.6(1H,m), 2.37(2H,t), 1.57(3H,d).

MS(%): m/e=210(M+, 21), 209(81), 96(100), 95(79), 69(67), 68(43).

(13) 1-[(2RS)-6-carboxy-2-methylhexyl]imidazole hydrochloride

The compound, having the following physical characteristics, was prepared from the ester compound [prepared as described in Example 5(4)].

IR: $\nu$=3600–2200, 1712, 1546, 1287, 1175, 1097, 836, 640 cm$^{-1}$.

NMR (D$_2$O solution): $\delta$=8.85(1H, m), 7.51(2H, m), 4.13(2H, m), 2.39(2H, t), 0.91(3H, d).

MS(%): m/e=210(M+, 29), 209(78), 82(100), 81(50), 69(30).

But the synthesis of the compounds (1), (2), (3), (4), (5), (6), (7), (8), (11) was carried out in the presence of methanol or ethanol, that of the compounds (1), (2), (5), (6), (7), (8) was carried out at 70° to 78° C., and the compounds (4), (5), (6), (7), (8), (11), (13) were not purified by recrystallization.

The present invention includes within its scope pharmaceutical compositions which comprise at least one new therapeutically useful imidazole derivative of general formula I or non-toxic acid addition salt thereof or, when R$^1$ in formula I represents a hydrogen atom, non-toxic salt thereof, together with a pharmaceutical carrier or coating. In clinical practice the new compounds of the present invention will normally be administered orally, parenterally or intrarectally.

Solid compositions for oral administration include compressed tablets, pills, dispersible powders and granules. In such solid compositions one or more of the active compounds is, or are, admixed with at least one inert diluent such as calcium carbonate, potato starch, alginic acid, lactose, mannitol, glucose or cacao butter. The compositions may also comprise, as is normal practice, additional substances other than inert diluents, e.g. lubricating agents such as nagnesium stearate. The tablets, if desired, may be coated and made into sugar-coated tablets, gelatin-coated tablets, enteric-coated tablets, film-coated tablets, or tablets coated with two or more layers.

Liquid compositions for oral administration include pharmaceutically-acceptable emulsions, solutions, suspensions, syrups and elixirs containing inert diluents commonly used in the art, such as water and liquid paraffin.

Besides inert diluents such compositions may also comprise adjuvants auch as wetting and suspending agents, and sweetening, flavouring, perfuming and preserving agents.

The compositions according to the invention for oral administration, also include capsules of absorbable material such as gelatin containing one or more of the active substances with or without the addition of diluents or excipients.

Solid compositions for intrarectal administration include suppositoties formulated in manner known per se and containing one or more of the active compounds.

Preparations according to the invention for parenteral administration include sterile aqueous or non-aqueous solutions, suspensions or emulsions. Examples of non-aqueous solvents or suspending media are propylene glycol, polyethylene glycol, ethanol, vegetable oils such as olive oil, and injectable organic esters such as ethyl oleate, sorbitan esters. These compositions may also include adjuvants such as preserving, wetting, emulsifying and dispersing agents. They may be sterilised, for example by filtration through a bacteia-retaining filter, by incorporation of sterilising agents in the compositions or irradiation. They may be also manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

The dosage of the compound of this invention is about 1 mg to 1,000 mg/body oral, or about 0.1 mg to 100 mg/body injected per day in multiple doses depending upon the disease which is being treated.

The following Examples illustrate pharmaceutical compositions according to the invention.

EXAMPLE 8

Ten g of (Z)-1-(7-carboxy-6-heptenyl)imidazole hydrochloride was admixed with 30 g of lactose, 15 g of Indian corn starch, 30 g of hydroxymethylcellulose, 2 g of calcium carboxymethylcellulose and 1 g of calcium stearate. The mixture was kneaded and shaped into 1,000 tablets. The tablets, thus obtained, were placed in a rotary coating tank and a 10% ethanolic solution of 1 g of polyvinylacetal diethylaminoacetate and 0.3 g of macrogol 6000 was added to the tablets and the mixture was stirred and dried.

EXAMPLE 9

Ten g of 1-[(7RS)-7-carboxyoctyl]imidazole hydrochloride was admixed with 30 g of lactose, 15 g of Indian corn starch, 30 g of hydroxymethylcellulose, 2 g of calcium carboxymethylcellulose and 1 g of calcium stearate. The mixture was kneaded and shaped into 1,000 tablets. The tablets, thus obtained, were placed in a rotary coating tank and a 10% ethanolic solution of 1 g of polyvinylacetal diethylaminoacetate and 0.3 g of macrogol 6000 was added to the tablets and the mixture was stirred and dried.

EXAMPLE 10

Five g of (Z)-1-(7-carboxy-6-heptenyl)imidazole hydrochloride and 10 g of chlorobutanol were dissolved in distilled water for injection to make the total amount 1,000 ml. One ml of the solution was poured into an ampoule to make 1,000 ampoules. The air was purged with nitrogen, and the ampoules were heated at 121° C. for 15 minutes to sterilize the solution to obtain an injectable preparation.

EXAMPLE 11

Five g of 1-[(7RS)-7-carboxyoctyl]imidazole hydrochloride and 10 g of chlorobutanol were dissolved in distilled water for injection to make the total amount 1,000 ml. One ml of the solution was poured into an ampoule to make 1,000 ampoules. The air was purged with nitrogen, and the ampoules were heated at 121° C. for 15 minutes to sterilize the solution to obtain an injectable preparation.

While the invention has been described in detail and with reference to specific embodiments thereof, it will be apparent to one skilled in the art that various changes and modifications can be made therein without departing from the spirit and scope thereof.

What is claimed is:

1. An imidazole derivative of the formula:

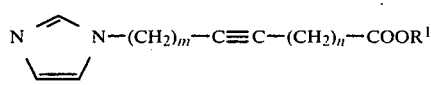

IB wherein $R^1$ represents a hydrogen atom, a non-toxic cation, or a straight- or branched-chain alkyl group containing from 1 to 12 carbon atoms, and m and n, which may be the same or different, each represent zero, or an integer of 1 to 10, or a non-toxic acid addition salt thereof.

2. An imidazole derivative or a non-toxic acid addition salt thereof according to claim 1 wherein $R^1$ represents a hydrogen atom, a non-toxic cation, or a straight- or branched-chain alkyl group containing from 1 to 4 carbon atoms.

3. An imidazole derivative or a non-toxic acid addition salt thereof according to claim 1 wherein $R^1$ represents a hydrogen atom, a non-toxic cation, or a methyl or ethyl group.

4. An imidazole derivative or a non-toxic acid addition salt thereof according to claim 1 wherein m+n represents zero, or an integer of 1 to 10.

5. An imidazole derivative or a non-toxic acid addition salt thereof according to claim 1 wherein m+n represents zero, or an integer of 1 to 6.

6. An imidazole derivative according to claim 1 which is 1-(7-methoxycarbonyl-6-heptynyl) imidazole or a non-toxic acid addition salt thereof.

7. An imidazole derivative according to claim 1 which is 1-(7-methoxycarbonyl-2-heptynyl) imidazole or a non-toxic acid addition salt thereof.

8. An imidazole derivative according to claim 1 which is 1-(7-carboxy-6-heptynyl) imidazole or (1) a non-toxic salt thereof when $R^1$ is a non-toxic cation or (2) a non-toxic acid addition salt thereof.

9. An imidazole derivative according to claim 1 which is 1-(7-carboxy-2-heptynyl) imidazole or (1) a non-toxic salt thereof when $R^1$ is a non-toxic cation or (2) a non-toxic acid addition salt thereof.

10. (E)-1-(7-ethoxycarbonyl-6-heptenyl) imidazole or a non-toxic acid addition salt thereof.

11. (Z)-1-(7-methoxycarbonyl-2-heptenyl) imidazole or a non-toxic acid addition salt thereof.

12. (Z)-1-(7-methoxycarbonyl-6-heptenyl) imidazole or a non-toxic acid addition salt thereof.

13. (E)-1-(7-carboxy-6-heptenyl) imidazole or a non-toxic carboxylic acid salt thereof or a non-toxic acid addition salt thereof.

14. (Z)-1-(7-carboxy-2-heptenyl) imidazole or a non-toxic carboxylic acid salt thereof or a non-toxic acid addition salt thereof.

15. (Z)-1-(7-carboxy-6-heptenyl) imidazole or a non-toxic carboxylic acid salt thereof or a non-toxic acid addition salt thereof.

16. A pharmaceutical composition for the treatment of inflammation, hypertension, thrombus, cerebral apoplexy, or asthma, which comprises, as active ingredient, an effective amount of at least one imidazole derivative as claimed in claim 1, or a non-toxic acid addition salt thereof, in association with a pharmaceutical carrier or coating.

* * * * *